United States Patent
Zuend et al.

(10) Patent No.: US 11,407,700 B2
(45) Date of Patent: Aug. 9, 2022

(54) PROCESS FOR PREPARING 2,3-UNSATURATED ALCOHOLS

(71) Applicant: BASF SE, Ludwigshafen am Rhein (DE)

(72) Inventors: Stephan Zuend, Fremont, CA (US); Andreas Keller, Ludwigshafen am Rhein (DE); Gabriele Gralla, Ludwigshafen am Rhein (DE); Wolfgang Krause, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 195 days.

(21) Appl. No.: 16/307,197

(22) PCT Filed: Jun. 6, 2017

(86) PCT No.: PCT/EP2017/063654
§ 371 (c)(1),
(2) Date: Dec. 5, 2018

(87) PCT Pub. No.: WO2017/211784
PCT Pub. Date: Dec. 14, 2017

(65) Prior Publication Data
US 2019/0263738 A1     Aug. 29, 2019

(30) Foreign Application Priority Data
Jun. 7, 2016  (EP) .................................... 16173352

(51) Int. Cl.
| | | |
|---|---|---|
| *C07C 29/141* | (2006.01) | |
| *B01J 23/89* | (2006.01) | |
| *B01J 37/00* | (2006.01) | |
| *B01J 37/02* | (2006.01) | |
| *B01J 37/04* | (2006.01) | |
| *B01J 37/06* | (2006.01) | |
| *C11B 9/00* | (2006.01) | |

(52) U.S. Cl.
CPC ......... *C07C 29/141* (2013.01); *B01J 23/8906* (2013.01); *B01J 37/009* (2013.01); *B01J 37/0236* (2013.01); *B01J 37/04* (2013.01); *B01J 37/06* (2013.01); *C11B 9/0015* (2013.01)

(58) Field of Classification Search
CPC .................................................... C07C 29/141
See application file for complete search history.

(56) References Cited

U.S. PATENT DOCUMENTS

| | | |
|---|---|---|
| 4,455,442 A | 6/1984 | Horner et al. |
| 4,465,787 A | 8/1984 | Horner et al. |
| 6,916,964 B2 | 7/2005 | Göbbel et al. |

(Continued)

FOREIGN PATENT DOCUMENTS

| | | |
|---|---|---|
| CN | 1200028 A | 11/1998 |
| EP | 0024648 A1 | 3/1981 |

(Continued)

OTHER PUBLICATIONS

Zsigmond et al. Journal of Catalysis 2004, 227, 428-435 (Year: 2004).*
Michalska et al. Platinum Metals Rev. 1974, 18, 65-73 (Year: 1974).*
International Preliminary Report on Patentability for PCT/EP2017/063654 dated Aug. 16, 2018.
International Search Report for PCT/EP2017/063654 dated Jul. 26, 2017.
Written Opinion of the International Searching Authority for PCT/EP2017/063654 dated Jul. 26, 2017.

(Continued)

*Primary Examiner* — Matthew P Coughlin
(74) *Attorney, Agent, or Firm* — Faegre Drinker Biddle & Reath LLP

(57) ABSTRACT

The present invention provides a process for preparing an unsaturated alcohol of the formula (I), wherein one of $R^1$ and $R^2$ is preferably $C_2$-$C_{10}$-alkyl or $C_2$-$C_{10}$-alkenyl containing one double bond and the other one is preferably hydrogen or methyl; $R^3$ is preferably hydrogen; which comprises subjecting an educt composition including at least 75% by weight of an unsaturated aldehyde of the formula (II) wherein $R^1$, $R^2$ and $R^3$ preferably have the above defined meanings, to a hydrogenation in the presence of a catalyst and a tertiary amine; wherein the tertiary amine is used in an amount ranging from 0.001 to 0.7% by weight, based on the total amount of the liquid reaction mixture. The invention further relates to the nerol compound obtainable by the inventive process, to a fragrance or aroma substance composition comprising the nerol compound obtainable by the inventive process, to a method for imparting and/or intensifying an odor or flavor of a product, and also to perfumed or aromatized products comprising a nerol compound obtainable by the inventive process.

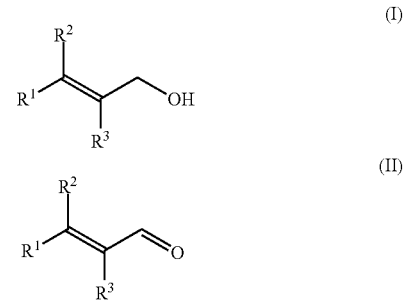

19 Claims, No Drawings

(56) References Cited

U.S. PATENT DOCUMENTS

| | | | |
|---|---|---|---|
| 7,101,824 B2 * | 9/2006 | Gerlach | B01J 21/18 |
| | | | 502/185 |
| 9,975,837 B2 | 5/2018 | Schelwies et al. | |
| 2003/0149310 A1 | 8/2003 | Gerlach et al. | |
| 2010/0193348 A1 | 8/2010 | Heydrich et al. | |
| 2011/0201819 A1 | 8/2011 | Shimizu | |
| 2011/0201820 A1 | 8/2011 | Shimizu | |
| 2017/0292084 A1 | 10/2017 | Stork et al. | |
| 2018/0170850 A1 | 6/2018 | Vautravers et al. | |
| 2018/0230176 A1 | 8/2018 | Puhl et al. | |
| 2018/0244598 A1 | 8/2018 | Schelwies et al. | |

FOREIGN PATENT DOCUMENTS

| | | |
|---|---|---|
| EP | 0071787 A2 | 2/1983 |
| EP | 1317959 A1 | 6/2003 |
| EP | 1318128 A2 | 6/2003 |
| EP | 1930075 A1 | 6/2008 |
| EP | 15188361.8 | 10/2015 |
| JP | 2003-245555 A | 9/2003 |
| JP | 2010-531323 A | 9/2010 |
| WO | 97/07778 A1 | 3/1997 |
| WO | 2007/029667 A1 | 3/2007 |
| WO | WO-2015004088 A1 | 1/2015 |
| WO | WO-2017211784 A1 | 12/2017 |

OTHER PUBLICATIONS

U.S. Appl. No. 16/060,260, filed Jun. 7, 2018, Vautravers et al.

Sonavane, S., et al., "Selective Reduction of C=O in $\alpha,\beta$-Unsaturated Carbonyls through Catalytic Hydrogen Transfer Reaction over Mixed Metal Oxides", SYNLETT, 2004, No. 1, pp. 146-148.

Bata et al., "Use of heterogenized metal complexes in hydrogenation reactions: comparison of hydrogenation and CTH reactions", Research on Chemical Intermediates, 41(12), 2015, pp. 9281-9294.

Gorgas et al., "Highly Efficient and Selective Hydrogenation of Aldehydes: A Well-Defined Fe(II) Catalyst Exhibits Noble-Metal Activity", ACS Catalysis, 6(4), 2016, pp. 2664-2672.

Zsigmond et al., "Selective hydrogenations on heterogenized ruthenium complexes", Journal of Catalysis, 227(2), 2004, pp. 428-435.

* cited by examiner

PROCESS FOR PREPARING 2,3-UNSATURATED ALCOHOLS

CROSS-REFERENCE TO RELATED APPLICATIONS

This application is a national stage application (under 35 U.S.C. § 371) of PCT/EP2017/063654, filed Jun. 6, 2017, which claims benefit of European Application No. 16173352.2, filed Jun. 7, 2016.

The present invention relates to a process for the selective catalytic hydrogenation of an α,β-unsaturated carbonyl compound, in particular neral or geranial, in the presence of a small amount of a tertiary amine to give the correspondingly unsaturated alcohol, in particular nerol or geraniol. The α,β-unsaturated carbonyl compound is introduced to the reaction as the major component of an educt composition, such as in particular citral. The invention further relates to the unsaturated alcohol obtainable by the inventive process, to a fragrance or aroma substance composition comprising a nerol compound obtainable by the inventive process, to a method for imparting and/or intensifying an odor or flavor of a product, and also to perfumed or flavored products comprising a nerol compound obtainable by the inventive process.

BACKGROUND OF THE INVENTION

Nerol and geraniol are valuable aroma chemicals that find use especially as odorants. They belong, together with citronellol and 2-phenylethanol, to the so-called rose alcohols, which are the principal constituents of rose oil and important aroma chemicals for creating a rose accord. Nerol often is of particular importance as it contributes fresh and green notes, whereas the scent of geraniol is rounder and more fruity.

As discussed in more detail below, known catalytic hydrogenations of α,β-unsaturated carbonyl compounds, such as in particular citral, yielding the respective unsaturated alcohols, such as in particular mixtures of nerol and geraniol, suffer from insufficient selectivity. They therefore result in high levels of unwanted side products arising, e.g., from over-hydrogenation or olefin isomerization. The processes of the prior art are particularly disadvantageous as they lead to substantial amounts of several side products having boiling points virtually equal to that of nerol, which makes it impossible to fully separate them from the intended product nerol by rectification and, thus, to obtain nerol in pure form. These side products are mainly citronellol on the one hand and the nerol isomers of formulae III to V on the other hand, which originate from over-hydrogenation and isomerization processes, respectively, which occur as side reactions during the hydrogenation reaction.

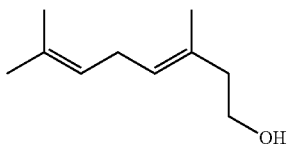
(III)

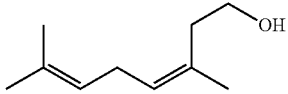
(IV)

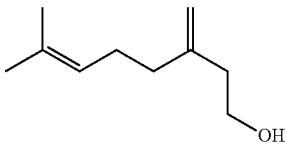
(V)

In addition, the hydrogenation processes of the prior art also often suffer from the disadvantage that they lead to formation of mixtures of nerol and geraniol. Whereas the formation of mixtures can be advantageous in certain situations, such as when the components of the mixture can be readily separated by a method such as rectification or when the mixture itself has desirable properties, the formation of mixtures of nerol and geraniol are disadvantageous for the production of nerol. As discussed above, nerol codistills with a variety of critical side products during rectification. Although geraniol may readily be separated from nerol by distillation, the presence of geraniol in the nerol mixture has the effect of decreasing the purity of the nerol obtained by rectification, as the codistilling impurities citronellol and nerol isomers III to V present in the reaction mixture become concentrated in the nerol fraction during the rectification.

The hydrogenation processes of the prior art are often also hampered in that they either do not allow at least near-complete conversion or are routinely terminated before full conversion is reached in order to reduce the levels of the aforementioned side products. However, incomplete conversion not only leads to lower yields but, in addition, to the negative effect that the obtained product is contaminated with considerable amounts of unreacted educt. Since neral and geranial can only be separated from nerol by highly elaborated rectification techniques, the conversion rate of the hydrogenation of citral should preferably be as high as possible. (Neral is also known in the art as cis-citral and citral B, while geranial is also known as trans-citral and citral A.)

In conclusion, there is an ongoing need for a hydrogenation process providing the conversion of α,β-unsaturated carbonyl compounds, such as in particular citral, to the corresponding unsaturated alcohols, such as in particular nerol and/or geraniol, with improved specificities and also higher conversion rates.

One measure of the selectivity of a hydrogenation starting from an educt composition that includes neral is the "nerol content after hydrogenation", which is defined as the percentage of the amount of nerol relative to the combined amounts of all compounds derived from the educt composition, consisting essentially of nerol, geraniol, citronellol, nerol isomers III to V, cis-citral, trans-citral, and citronellal. The "geraniol content after hydrogenation" is defined accordingly.

A second measure of the selectivity of a hydrogenation starting from an educt composition that includes neral is the "nerol purity attainable by rectification", which is defined as the percentage of the amount of nerol relative to the combined amounts of nerol, citronellol and the nerol isomers III to V within the raw product obtained after completion of the hydrogenation. Hence, if the final reaction mixture includes only small amounts of the side products that cannot be removed by rectification, i.e. citronellol and the nerol isomers III to V, the nerol purity attainable by rectification is close to 100%. Conversely, if the final reaction mixture includes moderate amounts of citronellol and nerol isomers III to V, the nerol purity attainable by rectification is substantially lower than 100%. In addition, if the final reaction mixture contains large amounts of other products, such as geraniol, cis-citral, or trans-citral, which are themselves separable from nerol by rectification, and small amounts of byproducts such as citronellol or nerol isomers III to V, the nerol purity attainable by rectification will also be substantially lower than 100%, because the non-separable side products become concentrated in the nerol fraction during rectification.

In an efficient process for the production of nerol, both the "nerol content after hydrogenation" and the "nerol purity attainable by rectification" should be as high as possible, ideally close to 100%.

In an attempt to increase the selectivity of the hydrogenation catalyst, the following processes of the prior art for converting citral into nerol and/or geraniol use activity-reducing and selectivity-enhancing bases. However, these processes are still afflicted with disadvantages for large scale preparations.

Sonavane et al. disclose the hydrogenation of neral in the presence of a CoO—$ZrO_2$ catalyst, 2-propanol as hydrogen donor and an equimolar amount of potassium hydroxide to give a modest 71% yield of nerol following purification by column chromatography (Synlett 2004, 1, 146-148). Both the moderate yield and the use of a column chromatography purification step make this method unsuitable for processes on a production scale.

US 2011/0201819 and US 2011/0201820 disclose the hydrogenation of α,β-unsaturated carbonyl compounds in the presence of a homogeneous copper catalyst, a mono- or diphosphine and a base to give the corresponding alcohol.

WO 2015/004088 discloses the transfer hydrogenation of citral to nerol/geraniol mixtures in the presence of a base and a sophisticated amino-amide-transition-metal complex as catalyst which is hardly suitable for a conversion on a production scale.

EP 1 930 075 discloses hydrogenation catalysts comprising an oxygen-containing gallium compound which is useful for the preparation of unsaturated alcohols from corresponding unsaturated aldehydes, such as citral. However, the conversion rates reported in EP 1 930 075 for the hydrogenation of citral to afford nerol/geraniol mixtures are rather mediocre.

EP 1 317 959, EP 0 024 648, EP 0 071 787 and EP 1 318 128 all disclose catalytic hydrogenations converting unsaturated carbonyl compounds into the correspondingly unsaturated alcohols using noble metal catalysts or ruthenium/iron catalysts. In all cases the hydrogenation is carried out in the presence of at least 1% by weight of a tertiary amine relative to the initial amount of the unsaturated carbonyl compound. However, all four documents do not address E/Z-isomerization side-reactions occurring during the hydrogenation which affect the double bond conjugated to the carbonyl group. Accordingly, these documents describe hydrogenations of citral to nerol/geraniol mixtures without observing the relation of the initial neral/geranial ratio to the nerol/geraniol ratio of the obtained mixture.

SUMMARY OF THE INVENTION

It is the object of the present invention to provide an economically attractive catalytic hydrogenation process that allows the preparation of 2,3-unsaturated alcohols, in particular nerol or geraniol, starting from the respective unsaturated aldehydes, in particular cis-citral or trans-citral. The process should be easy to perform and be suitable for industrial scale production. It should especially allow for selective conversion to the desired unsaturated alcohol at high rates and require only catalysts that are relatively inexpensive, easy to handle and recyclable.

The object is achieved by the process described in detail below.

The present invention provides a process for preparing an unsaturated alcohol of the formula (I),

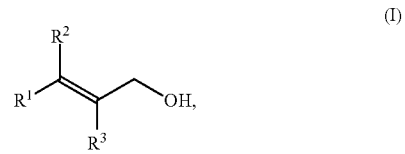

wherein
$R^1$ and $R^2$ are each independently from one another selected from hydrogen, $C_1$-$C_{20}$-alkyl which is unsubstituted or substituted with 1 to 5 identical or different radicals $R^4$, $C_2$-$C_{20}$-alkenyl which contains 1, 2, 3, 4 or 5 double bonds and is unsubstituted or substituted with 1 to 5 identical or different radicals $R^5$, aryl which is unsubstituted or substituted with 1 to 5 identical or different radicals $R^6$, and 3-, 4-, 5-, 6- or 7-membered saturated, partially unsaturated or aromatic heterocyclic rings containing as ring members 1, 2 or 3 heteroatoms which are, independently of each other, selected from N, $NR^a$, O and S, wherein the heterocyclic rings are unsubstituted or substituted with 1 to 5 identical or different radicals $R^6$; provided that $R^1$ and $R^2$ are different from each other;
$R^3$ is selected from hydrogen and $C_1$-$C_4$-alkyl;
$R^4$ is selected from hydroxyl, cyano, nitro, halogen, $C_3$-$C_7$-cycloalkyl, $C_1$-$C_4$-alkoxy, $C_1$-$C_4$-alkoxycarbonyl, $C_1$-$C_4$-alkylcarbonyloxy, —$NR^{7a}R^{7b}$ and aryl which may be unsubstituted or substituted with 1 to 5 identical or different radicals $R^6$;
$R^5$ is selected from hydroxyl, cyano, nitro, halogen, $C_1$-$C_4$-alkyl, $C_3$-$C_7$-cycloalkyl, $C_1$-$C_4$-alkoxy, $C_1$-$C_4$-alkoxycarbonyl, $C_1$-$C_4$-alkylcarbonyloxy, —$NR^{7a}R^{7b}$ and aryl which may be unsubstituted or substituted with 1 to 5 identical or different radicals $R^6$;
$R^6$ is selected from cyano, nitro, halogen, $C_1$-$C_4$-alkyl, $C_3$-$C_7$-cycloalkyl, $C_1$-$C_4$-alkoxy and —$NR^{7a}R^{7b}$;
$R^{7a}$ and $R^{7b}$ are each independently from one another selected from hydrogen, $C_1$-$C_6$-alkyl, $C_3$-$C_7$-cycloalkyl, $C_1$-$C_6$-alkoxy, $C_2$-$C_6$-alkenyl, $C(=O)R^8$, $C(=O)OR^9$, phenyl and benzyl; or
$R^{7a}$ and $R^{7b}$ together represent a $C_2$-$C_7$-alkylene chain which in combination with the nitrogen atom it is bonded to forms a 3-, 4-, 5-, 6-, 7- or 8-membered saturated, partly unsaturated or aromatic ring, wherein the alkylene chain may contain 1 or 2 heteroatoms which are, independently of each other, selected from O, S and $NR^b$, and where the alkylene chain may optionally be substituted with 1, 2, 3 or 4 identical or different radicals selected from halogen, $C_1$-$C_6$-alkyl, $C_3$-$C_7$-cycloalkyl and $C_1$-$C_6$-alkoxy;
$R^8$ is selected from hydrogen, $C_1$-$C_6$-alkyl, $C_2$-$C_6$-alkenyl, $C_3$-$C_7$-cycloalkyl, wherein the three last mentioned radicals may be unsubstituted or substituted with 1 or 2 identical or different radicals selected from hydroxyl and $C_1$-$C_4$-alkoxy;
$R^9$ is selected from $C_1$-$C_6$-alkyl, $C_2$-$C_6$-alkenyl, $C_3$-$C_7$-cycloalkyl, wherein the three last mentioned radicals may be unsubstituted or substituted with 1 or 2 identical or different radicals selected from hydroxyl and $C_1$-$C_4$-alkoxy;

$R^a$ is selected from $C_1$-$C_4$-alkyl, $C_3$-$C_7$-cycloalkyl and $C_1$-$C_4$-alkoxy;

$R^b$ is selected from hydrogen, $C_1$-$C_4$-alkyl, $C_3$-$C_7$-cycloalkyl and $C_1$-$C_4$-alkoxy;

which comprises subjecting an educt composition including at least 75% by weight of an unsaturated aldehyde of the formula (II)

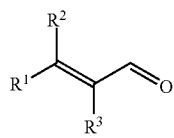
(II)

wherein $R^1$, $R^2$ and $R^3$ have the above defined meanings, to a hydrogenation in the presence of a catalyst and a tertiary amine;

wherein the tertiary amine is used in an amount ranging from 0.001 to 0.7% by weight, based on the total amount of the liquid reaction mixture.

EMBODIMENTS OF THE INVENTION

A first embodiment of the invention relates to a process for the preparation of an unsaturated alcohol of the formula (I),

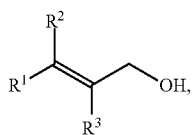
(I)

wherein $R^1$ and $R^2$ are each independently from one another selected from hydrogen, $C_1$-$C_{20}$-alkyl which is unsubstituted or substituted with 1 to 5 identical or different radicals $R^4$, $C_2$-$C_{20}$-alkenyl which contains 1, 2, 3, 4 or 5 double bonds and is unsubstituted or substituted with 1 to 5 identical or different radicals $R^5$, aryl which is unsubstituted or substituted with 1 to 5 identical or different radicals $R^6$, and 3-, 4-, 5-, 6- or 7-membered saturated, partially unsaturated or aromatic heterocyclic rings containing as ring members 1, 2 or 3 heteroatoms which are, independently of each other, selected from N, $NR^a$, O and S, wherein the heterocyclic rings are unsubstituted or substituted with 1 to 5 identical or different radicals $R^6$; provided that $R^1$ and $R^2$ are different from each other;

$R^3$ is selected from hydrogen and $C_1$-$C_4$-alkyl;

$R^4$ is selected from hydroxyl, cyano, nitro, halogen, $C_3$-$C_7$-cycloalkyl, $C_1$-$C_4$-alkoxy, $C_1$-$C_4$-alkoxycarbonyl, $C_1$-$C_4$-alkylcarbonyloxy, —$NR^{7a}R^{7b}$ and aryl which may be unsubstituted or substituted with 1 to 5 identical or different radicals $R^6$;

$R^5$ is selected from hydroxyl, cyano, nitro, halogen, $C_1$-$C_4$-alkyl, $C_3$-$C_7$-cycloalkyl, $C_1$-$C_4$-alkoxy, $C_1$-$C_4$-alkoxycarbonyl, $C_1$-$C_4$-alkylcarbonyloxy, —$NR^{7a}R^{7b}$ and aryl which may be unsubstituted or substituted with 1 to 5 identical or different radicals $R^6$;

$R^6$ is selected from cyano, nitro, halogen, $C_1$-$C_4$-alkyl, $C_3$-$C_7$-cycloalkyl, $C_1$-$C_4$-alkoxy and —$NR^{7a}R^{7b}$;

$R^{7a}$ and $R^{7b}$ are each independently from one another selected from hydrogen, $C_1$-$C_6$-alkyl, $C_3$-$C_7$-cycloalkyl, $C_1$-$C_6$-alkoxy, $C_2$-$C_6$-alkenyl, C(=O)$R^8$, C(=O)O$R^9$, phenyl and benzyl; or $R^{7a}$ and $R^{7b}$ together represent a $C_2$-$C_7$-alkylene chain which in combination with the nitrogen atom it is bonded to forms a 3-, 4-, 5-, 6-, 7- or 8-membered saturated, partly unsaturated or aromatic ring, wherein the alkylene chain may contain 1 or 2 heteroatoms which are, independently of each other, selected from O, S and $NR^b$, and where the alkylene chain may optionally be substituted with 1, 2, 3 or 4 identical or different radicals selected from halogen, $C_1$-$C_6$-alkyl, $C_3$-$C_7$-cycloalkyl and $C_1$-$C_6$-alkoxy;

$R^8$ is selected from hydrogen, $C_1$-$C_6$-alkyl, $C_2$-$C_6$-alkenyl, $C_3$-$C_7$-cycloalkyl, wherein the three last mentioned radicals may be unsubstituted or substituted with 1 or 2 identical or different radicals selected from hydroxyl and $C_1$-$C_4$-alkoxy;

$R^9$ is selected from $C_1$-$C_6$-alkyl, $C_2$-$C_6$-alkenyl, $C_3$-$C_7$-cycloalkyl, wherein the three last mentioned radicals may be unsubstituted or substituted with 1 or 2 identical or different radicals selected from hydroxyl and $C_1$-$C_4$-alkoxy;

$R^a$ is selected from $C_1$-$C_4$-alkyl, $C_3$-$C_7$-cycloalkyl and $C_1$-$C_4$-alkoxy;

$R^b$ is selected from hydrogen, $C_1$-$C_4$-alkyl, $C_3$-$C_7$-cycloalkyl and $C_1$-$C_4$-alkoxy;

which comprises subjecting an educt composition including at least 75% by weight of an unsaturated aldehyde of the formula (II)

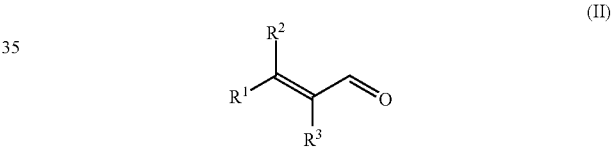
(II)

wherein $R^1$, $R^2$ and $R^3$ have the above defined meanings, to a hydrogenation in the presence of a catalyst and a tertiary amine;

wherein the tertiary amine is used in an amount ranging from 0.001 to less than 1% by weight, preferably in an amount ranging from 0.002 to 0.75% by weight, based on the total amount of the liquid reaction mixture.

A special variant of the first embodiment of the invention relates to a process for the preparation of an unsaturated alcohol of the formula (I),

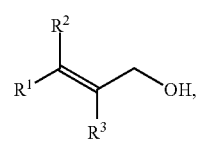
(I)

wherein $R^1$ and $R^2$ are each independently from one another selected from hydrogen, $C_1$-$C_{20}$-alkyl which is unsubstituted or substituted with 1 to 5 identical or different radicals $R^4$, $C_2$-$C_{20}$-alkenyl which contains 1, 2, 3, 4 or 5 double bonds and is unsubstituted or substituted with 1 to 5 identical or different radicals $R^5$, aryl which is unsubstituted or substituted with 1 to 5 identical or different radicals $R^6$, and 3-, 4-, 5-, 6- or 7-membered saturated, partially unsaturated or aromatic heterocyclic rings containing as ring members 1, 2 or 3 heteroatoms which are, independently of each other, selected from N, $NR^a$, O and S, wherein the heterocyclic rings are unsubstituted or substituted with 1 to 5 identical or different radicals $R^6$; provided that $R^1$ and $R^2$ are different from each other;

$R^3$ is selected from hydrogen and $C_1$-$C_4$-alkyl;

$R^4$ is selected from hydroxyl, cyano, nitro, halogen, $C_3$-$C_7$-cycloalkyl, $C_1$-$C_4$-alkoxy, $C_1$-$C_4$-alkoxycarbonyl, $C_1$-$C_4$-alkylcarbonyloxy, —$NR^{7a}R^{7b}$ and aryl which may be unsubstituted or substituted with 1 to 5 identical or different radicals $R^6$;

$R^5$ is selected from hydroxyl, cyano, nitro, halogen, $C_1$-$C_4$-alkyl, $C_3$-$C_7$-cycloalkyl, $C_1$-$C_4$-alkoxy, $C_1$-$C_4$-alkoxycarbonyl, $C_1$-$C_4$-alkylcarbonyloxy, —$NR^{7a}R^{7b}$ and aryl which may be unsubstituted or substituted with 1 to 5 identical or different radicals $R^6$;

$R^6$ is selected from cyano, nitro, halogen, $C_1$-$C_4$-alkyl, $C_3$-$C_7$-cycloalkyl, $C_1$-$C_4$-alkoxy and —$NR^{7a}R^{7b}$;

$R^{7a}$ and $R^{7b}$ are each independently from one another selected from hydrogen, $C_1$-$C_4$-alkyl, $C_3$-$C_7$-cycloalkyl, $C_1$-$C_6$-alkoxy, $C_2$-$C_6$-alkenyl, C(=O)$R^8$, C(=O)O$R^9$, phenyl and benzyl; or $R^{7a}$ and $R^{7b}$ together represent a $C_2$-$C_7$-alkylene chain which in combination with the nitrogen atom it is bonded to forms a 3-, 4-, 5-, 6-, 7- or 8-membered saturated, partly unsaturated or aromatic ring, wherein the alkylene chain may contain 1 or 2 heteroatoms which are, independently of each other, selected from O, S and $NR^b$, and where the alkylene chain may optionally be substituted with 1, 2, 3 or 4 identical or different radicals selected from halogen, $C_1$-$C_6$-alkyl, $C_3$-$C_7$-cycloalkyl and $C_1$-$C_6$-alkoxy;

$R^8$ is selected from hydrogen, $C_1$-$C_6$-alkyl, $C_2$-$C_6$-alkenyl, $C_3$-$C_7$-cycloalkyl, wherein the three last mentioned radicals may be unsubstituted or substituted with 1 or 2 identical or different radicals selected from hydroxyl and $C_1$-$C_4$-alkoxy;

$R^9$ is selected from $C_1$-$C_6$-alkyl, $C_2$-$C_6$-alkenyl, $C_3$-$C_7$-cycloalkyl, wherein the three last mentioned radicals may be unsubstituted or substituted with 1 or 2 identical or different radicals selected from hydroxyl and $C_1$-$C_4$-alkoxy;

$R^a$ is selected from $C_1$-$C_4$-alkyl, $C_3$-$C_7$-cycloalkyl and $C_1$-$C_4$-alkoxy;

$R^b$ is selected from hydrogen, $C_1$-$C_4$-alkyl, $C_3$-$C_7$-cycloalkyl and $C_1$-$C_4$-alkoxy;

which comprises subjecting an educt composition including at least 75% by weight of an unsaturated aldehyde of the formula (II)

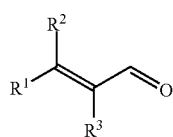

(II)

wherein $R^1$, $R^2$ and $R^3$ have the above defined meanings, to a hydrogenation in the presence of a catalyst and a tertiary amine;

wherein the tertiary amine is used in an amount ranging from 0.001 to 0.7% by weight, based on the total amount of the liquid reaction mixture.

A second embodiment of the invention relates to the process according to embodiment 1, wherein the catalyst is a heterogeneous catalyst.

A third embodiment of the invention relates to the process according to embodiment 2, wherein the heterogeneous catalyst is a supported catalyst which comprises ruthenium as supported on an inert support material.

A fourth embodiment of the invention relates to the process according to embodiment 3, wherein the supported catalyst additionally comprises iron.

A fifth embodiment of the invention relates to the process according to embodiment 3 or 4, wherein the supported catalyst has a ruthenium content in the range of 0.1 to 10% by weight, based on the dry weight of the catalyst.

A sixth embodiment of the invention relates to the process according to embodiment 4 or 5, wherein the supported catalyst has an iron content in the range of 0.1 to 5% by weight, based on the dry weight of the catalyst.

A seventh embodiment of the invention relates to the process according to any one of embodiments 3 to 6, wherein the supported catalyst is prepared by a process comprising the following steps:

a) suspending the support material in water, b) simultaneously adding ruthenium and optionally iron in the form of solutions of their metal salts, c) precipitating ruthenium and, if applicable, iron essentially in the form of their hydroxides onto the support by the addition of a base, d) separating the loaded support from the aqueous phase of the suspension, e) drying the loaded support, f) subjecting the loaded support to hydrogenation conditions at a temperature of below 600° C., and g) conditioning the obtained catalyst under a liquid having low flammability, or passivating the obtained catalyst with a dilute oxygen stream, or passivating the obtained catalyst with a dilute oxygen stream and conditioning the catalyst under a liquid having low flammability.

A eighth embodiment of the invention relates to the process according to embodiment 7, wherein the reduction in step f) is carried out at a temperature in the range of 100 to below 600° C., preferably 120 to below 400° C. and in particular 150 to 250° C.

A ninth embodiment of the invention relates to the process according to any one of embodiments 3 to 8, wherein the support material is selected from carbon, alumina and silica, and preferably is carbon.

A tenth embodiment of the invention relates to the process according to any one of the preceding embodiments, wherein the tertiary amine is used in an amount ranging from 0.005 to 0.5% by weight and preferably 0.01 to 0.2% by weight, based on the total amount of the liquid reaction mixture.

A eleventh embodiment of the invention relates to the process according to any one of the preceding embodiments, wherein the tertiary amine is selected from tri($C_1$-$C_{20}$-alkyl) amines and preferably is trimethylamine.

A twelfth embodiment of the invention relates to the process according to any one of the preceding embodiments, wherein the hydrogenation is carried out in the presence of a protic organic solvent which is preferably selected from $C_1$-$C_8$-alkanoles and in particular is methanol.

A thirteenth embodiment of the invention relates to the process according to any one of the preceding embodiments, wherein the hydrogenation is carried out at a temperature in the range of 40 to 150° C. and preferably 50 to 90° C.

A fourteenth embodiment of the invention relates to the process according to any one of the preceding embodiments, wherein the hydrogenation is carried out at a pressure in the range of 10 to 200 bar and preferably 20 to 100 bar.

A fifteenth embodiment of the invention relates to the process according to any one of the preceding embodiments, wherein the hydrogenation is carried out discontinuously.

A sixteenth embodiment of the invention relates to the process according to embodiment 15, wherein the heterogeneous catalyst used in the hydrogenation is a recycled catalyst that had been used in at least one previous hydrogenation reaction.

A seventeenth embodiment of the invention relates to the process according to embodiment 15 or 16, wherein the educt composition is contacted with the tertiary amine only after the hydrogenation vessel containing the catalyst was purged with hydrogen gas and the desired reaction pressure and temperature within the vessel have been reached.

A eighteenth embodiment of the invention relates to the process according to any one of c embodiments 15 to 17, wherein the educt composition is added to the reaction mixture continuously or intermittently over the course of the hydrogenation reaction.

A nineteenth embodiment of the invention relates to the process according to any one of the preceding embodiments, wherein
one of $R^1$ and $R^2$ is $C_2$-$C_{10}$-alkyl or $C_2$-$C_{10}$-alkenyl containing one double bond and the other one is hydrogen or methyl; and
$R^3$ is hydrogen.

A twentieth embodiment of the invention relates to the process according to any one of the preceding embodiments, wherein
one of $R^1$ and $R^2$ is $C_4$-$C_{10}$-alkenyl containing one double bond and the other one is methyl; and
$R^3$ is hydrogen.

A twenty-first embodiment of the invention relates to the process according to any one of the preceding embodiments, wherein the unsaturated alcohol of the formula (I) is geraniol and the unsaturated aldehyde of the formula (II) is geranial.

A twenty-second embodiment of the invention relates to the process according to any one of embodiments 1 to 20, wherein the unsaturated alcohol of the formula (I) is nerol and the unsaturated aldehyde of the formula (II) is neral.

A twenty-third embodiment of the invention relates to the process according to embodiment 21 or 22, wherein the educt composition is citral.

A twenty-fourth embodiment of the invention relates to the process according to embodiment 23, wherein the citral comprises at least 90% and preferably at least 99% by weight of neral.

A twenty-fifth embodiment of the invention relates to the process according to embodiment 24, wherein the raw product obtained has a nerol content after hydrogenation of more than 85% by weight, preferably more than 90% by weight, and a geraniol content after hydrogenation of not more than 9% by weight, preferably not more than 6% by weight.

A twenty-sixth embodiment of the invention relates to the process according to any one of embodiments 22 to 25, wherein the raw product obtained after the hydrogenation is subjected to a rectification step affording nerol in a purity of above 90%, preferably above 94%, and in particular above 96%.

A twenty-seventh embodiment of the invention relates to the process according to any one of embodiments 22 to 26, wherein the raw product obtained after the hydrogenation is subjected to a rectification step affording a nerol compound having a level of the by-products citronellol and nerol isomers in total of less than 10% by weight, preferably less than 6% by weight, and in particular from 2 to 4% by weight.

A twenty-eighth embodiment of the invention relates to the nerol compound obtainable by the process according to embodiment 27, which comprises 94 to 98% by weight, preferably 96 to 98% by weight, of nerol and 2 to 6% by weight, preferably 2 to 4% by weight, of the by-products citronellol and nerol isomers together, relative in each case to the total weight of the nerol compound.

A twenty-ninth embodiment of the invention relates to the use of the nerol compound according to embodiment 28 as aroma chemical, in particular as odorant.

A thirtieth embodiment of the invention relates to the use according to embodiment 29 in compositions selected from perfumes, detergents and cleaners, cosmetic compositions, bodycare compositions, hygiene articles, products for oral and dental hygiene, scent dispensers and fragrances.

A thirty-first embodiment of the invention relates to the use according to embodiment 29 or 30 for producing a radiant and impactful rose-floral note that is fresh, citrusy, powdery, and smooth.

A thirty-second embodiment of the invention relates to a fragrance or aroma substance composition, comprising
a) the nerol compound according to embodiment 28,
b) optionally at least one further aroma chemical different from component a), and
c) optionally at least one diluent,
with the proviso that the composition comprises at least one of the components b) or c).

A thirty-third embodiment of the invention relates to the composition according to embodiment 32, comprising the component a) in a weight fraction of from 0.1 to 70% by weight, preferably 1 to 50% by weight, based on the total weight of the composition.

A thirty-fourth embodiment of the invention relates to a method for imparting and/or intensifying an odor or flavor of a product with a fresh, citrusy, powdery and smooth rose-floral note, in which the product is brought into contact with an organoleptically effective amount of the nerol compound according to embodiment 28.

A thirty-fifth embodiment of the invention relates to a perfumed or aromatized product, comprising an organoleptically effective amount of the nerol compound according to embodiment 28 or comprising an organoleptically effective amount of a fragrance or aroma substance composition as defined in either of embodiments 32 and 33.

A thirty-sixth embodiment of the invention relates to the product according to embodiment 35, selected from scent dispensers and fragrance perfumes, detergents and cleaners, cosmetic compositions, bodycare compositions, hygiene articles, products for oral and dental hygiene, pharmaceutical compositions and crop protection compositions.

DETAILED DESCRIPTION OF THE INVENTION

The process according to the invention is associated with a series of advantages. Firstly, starting from educt compositions mainly comprising unsaturated aldehydes of the formula II it affords the unsaturated alcohols of the formula I in high yields and low levels of side products. Particularly, the formation of those side products that cannot be removed by rectification, i.e. citronellol and the nerol isomers, is markedly reduced. Also, the process does not require sophisticated hydrogenation catalysts but only readily accessible ones and, in addition, enables the catalyst to maintain its activity over many re-use cycles. In conclusion, the process of the invention allows for the easy, efficient and economical production of the desired alcohols of the formula I.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" as used herein, refers to fluoro, chloro, bromo or iodo.

The term "$C_1$-$C_n$-alkyl" as used herein, and also in $C_1$-$C_4$-alkylcarbonyloxy, refers to a branched or unbranched saturated hydrocarbon group having 1 to n, e.g. 1 to 10 carbon atoms, preferably 1 to 6 carbon atoms and in particular 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_n$-alkoxy" is a $C_1$-$C_n$-alkyl group, as defined above, attached via an oxygen atom. $C_1$-$C_2$-alkoxy is methoxy or ethoxy. $C_1$-$C_4$-alkoxy is, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-alkoxy includes the meanings given for $C_1$-$C_4$-alkoxy and also includes, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

The term "$C_2$-$C_n$-alkenyl" as used herein denotes a linear or branched ethylenically unsaturated hydrocarbon group having 2 to m, e.g. 2 to 20 or 2 to 6 carbon atoms and a C=C-double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_{20}$-alkenyl which contains 1, 2, 3, 4 or 5 double bonds" as used herein denotes a linear or branched ethylenically unsaturated hydrocarbon group having 2 to 20 carbon atoms and 1 to up to 5 C=C-double bonds wherein each of the carbon atoms is involved not more than 1 double bond. $C_2$-$C_{20}$-alkenyl containing one double bond is for example one of those mentioned above for $C_2$-$C_n$-alkenyl, $C_2$-$C_{20}$-alkenyl containing two double bonds is for example 1,3-butadienyl, 1,4-pentadienyl, 1,3-pentadienyl, 2,4-pentadienyl, 2-methyl-1,3-butadienyl, 1,5-hexadienyl, 1,4-hexadienyl, 1,3-hexadienyl, 2,5-hexadienyl, 3,5-hexadienyl, 2,4-hexadienyl, 2-methyl-1,3-pentadienyl or 4-methyl-1,3-pentadienyl, $C_2$-$C_{20}$-alkenyl containing three double bonds is for example 1,3,5-hexatrienyl, 1,3,6-heptatrienyl, 1,4,7-octatrienyl or 2-methyl-1,3,5-hexatrienyl, $C_2$-$C_{20}$-alkenyl containing four double bonds is for example 1,3,5,7-octatetraenyl, 1,3,5,8-nonatetraenyl, 1,4,7,10-undecatetraenyl or 2-ethyl-1,3,6,8-nonatetraenyl, and $C_2$-$C_{20}$-alkenyl containing five double bonds is for example 1,3,5,7,9-decapentaenyl, 1,4,6,8,10-undecapentaenyl, 1,4,6,9,11-dodecapentaenyl or 2-ethenyl-1,3,5,8-nonatetraenyl.

The term "$C_3$-$C_7$-cycloalkyl" as used herein refers to a monocyclic and bicyclic 3- to 7-membered saturated cycloaliphatic radical, e.g. cyclopropyl, cyclobutyl, cyclopentyl, cyclohexyl, cycloheptyl, bicyclo[2.2.1]heptyl and bicyclo[3.1.1]heptyl. Preferably, the term cycloalkyl denotes a monocyclic saturated hydrocarbon radical.

The term "$C_1$-$C_4$-alkoxycarbonyl" is a $C_1$-$C_4$-alkoxy group, as defined above, attached via a carbonyl group. $C_1$-$C_2$-Alkoxycarbonyl is methoxycarbonyl or ethoxycarbonyl. $C_1$-$C_4$-Alkoxy is, for example, methoxycarbonyl, ethoxycarbonyl, n-propoxycarbonyl, 1-methylethoxycarbonyl, butoxycarbonyl, 1-methylpropoxycarbonyl, 2-methylpropoxycarbonyl or 1,1-dimethylethoxycarbonyl.

The term "$C_1$-$C_4$-alkylcarbonyloxy" is a $C_1$-$C_4$-alkyl group, as defined above, attached via a carbonyloxy group (—C(=O)—O—). $C_1$-$C_2$-alkylcarbonyloxy is methylcarbonyloxy or ethylcarbonyloxy. $C_1$-$C_4$-alkylcarbonyloxy is, for example, methylcarbonyloxy, ethylcarbonyloxy, n-propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy.

The term "aryl" as used herein refers to an aromatic hydrocarbon radical such as naphthyl or in particular phenyl.

The term "3-, 4-, 5-, 6- or 7-membered saturated, partially unsaturated or aromatic heterocyclic ring containing as ring members 1, 2 or 3 heteroatoms which are, independently from each other, selected from N, $NR^a$, O and S", as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic rings, also termed heteroaromatic rings, heteroaryl or hetaryl, include: 2-furyl, 3-furyl, 2-thienyl, 3-thienyl, 2-pyrrolyl, 3-pyrrolyl, 3-pyrazolyl, 4-pyrazo¬lyl, 5-pyrazolyl, 2-oxazolyl, 4-oxazolyl, 5-oxazolyl, 2-thiazolyl, 4 thiazolyl, 5-thiazo¬lyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_1$-$C_7$-alkylene chain" is divalent branched or preferably non-branched or linear saturated aliphatic chain having 1 to 7 carbon atoms, for example —$CH_2$—, —$CH_2CH_2$—, —$CH(CH_3)$—, —$CH_2CH_2CH_2$—, —$CH(CH_3)CH_2$—, —$CH_2CH(CH_3)$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—.

The term "$C_2$-$C_7$-alkylene chain which in combination with the nitrogen atom it is bonded to forms a 3-, 4-, 5-, 6-, 7- or 8-membered saturated, partly unsaturated or aromatic ring, wherein the alkylene chain may contain 1 or 2 heteroatoms which are, independently of each other, selected from O, S and $NR^b$", as used herein refers to monocyclic radicals, the monocyclic radicals being saturated, partially unsaturated or aromatic. The heterocyclic radical is attached to the remainder of the molecule via the nitrogen to which the $C_2$-$C_7$-alkylene chain is bonded to and which, consequently, is a ring member. Examples are those of heterocyclic rings mentioned above for "3-, 4-, 5-, 6- or 7-membered saturated, partially unsaturated or aromatic heterocyclic ring containing as ring members 1, 2 or 3 heteroatoms which are, independently from each other, selected from N, $NR^a$, O and S" that are attached via a nitrogen atom.

The term "liquid reaction mixture" as used herein refers to the liquid part of the reaction mixture which includes all liquid components as well as any solid components dissolved therein, such as solvents as well as liquid or dissolved educts, products and by-products.

The term "citral" as used herein refers to a composition consisting largely, i.e. to an extent of usually at least 90% by weight, preferably at least 95% by weight and in particular at least 98% by weight, of a mixture of neral and geranial in any proportion.

A preferred embodiment of the invention relates to the preparation of compounds of the formula I, wherein:
one of $R^1$ and $R^2$ is selected from:
  $C_1$-$C_{20}$-alkyl which is unsubstituted or substituted with 1 to 5 identical or different radicals selected from hydroxyl, cyano, nitro, halogen, $C_3$-$C_7$-cycloalkyl and $C_1$-$C_4$-alkoxy,
  $C_2$-$C_{20}$-alkenyl which contains 1, 2, 3 or 4 double bonds and is unsubstituted or substituted with 1 to 5 identical or different radicals selected from hydroxyl, cyano, nitro, halogen, $C_1$-$C_4$-alkyl, $C_3$-$C_7$-cycloalkyl and $C_1$-$C_4$-alkoxy, and
  aryl which is unsubstituted or substituted with 1 to 5 identical or different radicals selected from hydroxyl, cyano, nitro, halogen, $C_1$-$C_4$-alkyl, $C_3$-$C_7$-cycloalkyl and $C_1$-$C_4$-alkoxy;
the other one of $R^1$ and $R^2$ is selected from:
hydrogen and
  $C_1$-$C_{10}$-alkyl which is unsubstituted or substituted with 1 to 3 identical or different radicals selected from hydroxyl, cyano, nitro, halogen, $C_3$-$C_7$-cycloalkyl and $C_1$-$C_4$-alkoxy; and
$R^3$ is selected from hydrogen and $C_1$-$C_4$-alkyl.

Another preferred embodiment of the invention relates to the preparation of compounds of the formula I, wherein:
one of $R^1$ and $R^2$ is selected from:
  $C_1$-$C_{15}$-alkyl which is unsubstituted or substituted with 1 to 3 identical or different radicals selected from hydroxyl, halogen, $C_3$-$C_6$-cycloalkyl and $C_1$-$C_4$-alkoxy, and $C_2$-$C_{15}$-alkenyl which contains 1, 2 or 3 double bonds and is unsubstituted or substituted with 1 to 3 identical or different radicals selected from hydroxyl, halogen, $C_1$-$C_4$-alkyl and $C_1$-$C_3$-alkoxy;
the other one of $R^1$ and $R^2$ is selected from hydrogen and unsubstituted $C_1$-$C_4$-alkyl; and
$R^3$ is selected from hydrogen and $C_1$-$C_4$-alkyl.

A further preferred embodiment of the invention relates to the preparation of compounds of the formula I, wherein:
one of $R^1$ and $R^2$ is $C_2$-$C_{10}$-alkyl or $C_2$-$C_{10}$-alkenyl containing one double bond;
the other one is hydrogen or methyl; and
$R^3$ is hydrogen.

A particularly preferred embodiment of the invention relates to the preparation of compounds of the formula I, wherein:
one of $R^1$ and $R^2$ is $C_4$-$C_{10}$-alkenyl containing one double bond;
the other one is methyl; and
$R^3$ is hydrogen.

In accordance with each of the four aforementioned embodiments the respective variables $R^1$, $R^2$ and $R^3$ of the unsaturated aldehyde of formula II have the same preferred meanings.

A specifically preferred embodiment of the invention, hereafter called embodiment A, relates to a process wherein the unsaturated alcohol of the formula I is geraniol and the unsaturated aldehyde of the formula II is geranial.

Another specifically preferred embodiment of the invention, hereafter called embodiment B, relates to a process wherein the unsaturated alcohol of the formula I is nerol and the unsaturated aldehyde of the formula II is neral.

In the process of embodiment A as well as in the process of embodiment B preferably citral is used as the educt composition.

In the process according to embodiment A it is preferred to use citral as educt composition that comprises as the unsaturated aldehyde of formula II at least 80% by weight, preferably at least 85% by weight, more preferably at least 90% by weight, even more preferably at least 95% by weight, particularly at least 98% by weight and specifically at least 99% by weight of geranial. In the process of embodiment A it is particularly preferred to use citral which comprises at least 80% by weight of geranial and at least 15% by weight of neral, more preferably at least 90% by weight of geranial and at least 5% by weight of neral, even more preferably at least 95% by weight of geranial and up to 5% by weight of neral, particularly at least 98% by weight of geranial and up to 2% by weight of neral and specifically at least 99% by weight of geranial and up to 1% by weight of neral.

In the processes according to embodiment B it is preferred to use citral as educt composition that comprises as the unsaturated aldehyde of formula II at least 80% by weight, preferably at least 85% by weight, more preferably at least 90% by weight, even more preferably at least 95% by weight, particularly at least 98% by weight and specifically at least 99% by weight of neral. In the process of embodiment B it is particularly preferred to use citral which comprises at least 80% by weight of neral and at least 15% by weight of geranial, more preferably at least 90% by weight of neral and at least 5% by weight of geranial, even more preferably at least 95% by weight of neral and up to 5% by weight of geranial, particularly at least 98% by weight of neral and up to 2% by weight of geranial and specifically at least 99% by weight of neral and up to 1% by weight of geranial.

Being configurable to a continuous, semicontinuous or batchwise manner, the hydrogenation of the inventive process for preparing 2,3-unsaturated alcohols of the formula I is performed in a reaction vessel customary for such a reaction. Examples of suitable reaction vessels are autoclaves and bubble columns of the type described in EP 1 318 128 which are typically equipped with a heating device, a stirring apparatus for mixing the reactants and a thermometer for controlling the temperature of the reaction mixture.

The process according to the present invention comprises the conversion to the 2,3-unsaturated alcohol of the formula I via a catalytic hydrogenation of the corresponding aldehyde of the formula II. The conversion is effected by reacting the alcohol I with hydrogen as reducing agent in the presence of a catalyst and a tertiary amine under suitable reaction conditions.

The catalyst used in the process of the invention may in principle be any catalyst capable of catalyzing the conversion of an aldehyde into the corresponding alcohol via a hydrogenation reaction using gaseous hydrogen as hydrogen source. It is typically either a homogeneous or heterogeneous catalyst which comprises at least one transition metal, in particular one from the groups IVB, VIIIB or IB of the Periodic Table (CAS version), for example zirconium, palladium, platinum, iron, cobalt, nickel, rhodium, iridium, ruthenium or copper. These metals may be present in the catalyst, either alone or in combination, in the form of one of their salts, oxides or complexes, or, alternatively in metallic form.

In one embodiment of the invention the catalyst comprises as active metal ruthenium in its metallic form, in the form of one of its oxides or salts, or mixtures thereof. The catalyst may include not only ruthenium but also one or more additional transition metals. Thus, according to a particularly preferred aspect of this embodiment the catalyst besides ruthenium additionally comprises iron as a further active metal in its metallic form, in the form of one of its oxides or salts, or mixtures thereof.

The weight data with regard to ruthenium and other metals refer to the weight of the metal, regardless whether the metals are present in metallic form or in the form of their oxides or salts.

In a preferred embodiment of the invention the catalyst is a heterogeneous catalyst, which typically is either a full catalyst or a supported catalyst. A full catalyst is a catalyst, where the active metal in its elementary or oxidic form makes up at least 50% by weight in particular at least 80% by weight of the catalyst in its active form. A supported catalyst is a catalyst where the active metal is supported on an inert support material. In a supported catalyst the amount of active metal is principally in the range from 0.05% by weight to 15% by weight, preferably from 0.1 to 10% by weight, in particular from 1 to 7% by weight, based on the dry weight of the catalyst. Suitable support materials include carbon, such as activated carbon, silicon carbide, silica, titanium dioxide, zirconium dioxide, alumina and alumosilicates, such as zeolites. Preferably, the support material has a specific surface area, determined by $N_2$ adsorption according to DIN 66131, of at least 10 m$^2$/g, in particular from 50 to 2000 m$^2$/g. The support material is preferably selected from the group consisting of carbon, alumina and silica, and in particular is carbon, such as specifically activated carbon.

In a preferred embodiment of the invention the heterogeneous catalyst, as preferably used in the process according to the invention, is a supported catalyst comprising ruthenium that is supported on an inert support material. According to a particularly preferred aspect of this embodiment the supported catalyst additionally comprises a further transition metal that is also supported on the support material. The further transition metal is preferably iron. In addition, the ruthenium content of the supported catalyst is preferably in the range of 0.1 to 10% by weight, in particular of 1 to 7% by weight, while its iron content, if iron is included in the catalyst, is preferably in the range of 0.1 to 5% by weight, in particular of 0.1 to 3% by weight, based in each case on the dry weight of the catalyst.

The supported catalyst can be used in the form of a powder. In general, such a powder has particle sizes in the range from 1 to 200 µm, in particular 1 to 100 µm. Powdery catalysts are suitable especially when the catalyst is suspended in the reaction mixture to be hydrogenated. In the case the catalyst is used in a fixed catalyst bed, it is customary to employ shaped bodies, which may have, for example, the shape of spheres, tablets, cylinders, strands, rings or hollow cylinders, stars, spalls and the like. The dimensions of these shaped bodies vary typically within the range from 0.5 mm to 25 mm. Frequently, catalyst extrudates with extrudate diameters of 1 to 5 mm and extrudate lengths of 2 to 25 mm are used.

In a particularly preferred embodiment of the invention the catalyst used in the process according to the invention comprises both ruthenium and iron as supported on a support material which is a carbon carrier, in particular activated carbon. Such a catalyst is typically used in powder form.

The catalysts according to the invention that comprise one or more transition metals can be prepared by customary processes well-known in the art. The herein preferred supported catalysts comprising ruthenium and optionally iron are preferably obtained by the process disclosed in EP 1 317 959 and especially by the process disclosed in the unpublished European patent application 15188361.8 filed on Oct. 5, 2015. Both documents are incorporated herein by reference. In summary said processes comprising the following steps:
a) suspending the support material in water,
b) simultaneously adding ruthenium and optionally iron in the form of solutions of their metal salts,
c) precipitating ruthenium and, if applicable, iron essentially in the form of their hydroxides onto the support by the addition of a base,
d) separating the loaded support from the aqueous phase of the suspension,
e) drying the loaded support,
f) subjecting the loaded support to hydrogenation conditions at a temperature of below 600° C., and
g) conditioning the obtained catalyst under a liquid having low flammability, or passivating the obtained catalyst with a dilute oxygen stream, or passivating the obtained catalyst with a dilute oxygen stream and conditioning the catalyst under a liquid having low flammability.

The support material employed in step a) is typically in a finely divided form, such as for example powdered activated carbon. The aqueous suspension obtained in step a) may be used in step b) as is or may possibly be adjusted to a pH value below 7, in particular below 6, by adding an acid, e.g. nitric acid, or to a pH value above 7, in particular above 8, by adding a base, such as sodium hydroxide.

In step b) the addition of the ruthenium salt and, if applicable, the iron salt is preferably carried out at an elevated suspension temperature, in particular at a temperature of 50 to 95° C., and specifically at a temperature of 70 to 90° C. Suitable salts of ruthenium and iron include their chlorides, nitrates, nitrosylnitrates, acetates, oxides, hydroxides and acetylacetonates, such as in particular ruthenium chloride, ruthenium nitrosyl nitrate, iron chloride and iron nitrate.

In step c) the base, such as for example sodium carbonate, sodium hydrogencarbonate, ammonium carbonate, ammonia, urea, sodium hydroxide, potassium hydroxide or lithium hydroxide, in particular sodium hydroxide, is typically slowly added to the suspension obtained in step b) until a pH value in the range of 6 to 14, preferably in the range of 8 to 12 and in particular in the range of 8 to 10 is reached. The base is preferably added to the suspension having an elevated temperature, in particular a temperature of 50 to 95° C., and specifically a temperature of 70 to 90° C.

In step d) the loaded support is preferably separated by filtration and the obtained filter cake is then dried in step e) usually under reduced pressure or an inert gas atmosphere.

In step f) the material obtained in step e) is reduced in a hydrogen stream, possibly diluted with an inert gas, such as nitrogen. The hydrogen content of the hydrogen stream is typically in the range of 5 to 100% by volume, preferably 5 to 50% by volume and in particular 5 to 25% by volume.

The reduction in step f) is preferably carried out at a temperature in the range of 100 to below 600° C., preferably 150 to below 550° C., and in particular 180 to 520° C.

In one embodiment of the invention the reduction in step f) is carried out at a temperature in the range of 400 to below 600° C., preferably 450 to 550° C., and in particular 480 to 520° C.

In a preferred embodiment of the invention the reduction in step f) is carried out at a temperature of 100 to 400° C., preferably 120 to 300, in particular 150 to 250° C., especially 180 to 220° C., and specifically 190 to 210° C.

In step g) the catalyst obtained in step f) may be conditioned under a low flammability liquid, such as water, typically after cooling it to temperatures below 40° C. Alternatively or in addition to such a conditioning a passivation process can be carried out in step f). According to one embodiment of the present invention passivation is effected by means of a diluted oxygen stream usually at a temperature in the range of 10 to 30° C., such as ambient temperature. Preferred diluted oxygen streams have an oxygen content of below 50% by volume, in particular below 25% by volume, particularly preferred below 10% by volume, especially below 5% by volume and specifically of about 1% by volume. For diluting oxygen typically an inert gas, such as nitrogen, helium, neon, argon or carbon dioxide, and preferably nitrogen, is used.

The preparation of a fixed bed catalyst is carried out similarly to the process described above for the suspension catalyst, except that in step a) shaped bodies such as extrudates, strands, spheres, or the like, are used in place of the powdered material. The characteristic dimensions of these bodies (diameter, length, etc.) are generally above 1 mm. When the bodies are dispersed in water, care should be taken to minimize the mechanical stress they are exposed to, in order to minimize attrition. It is advantageous to wash the bodies with water before using them as catalysts, in order to separate weakly adhering fine particles.

The tertiary amine used in the process of the invention may in principle be any tertiary amine, preference is given, however, to those that are readily separable from the product of formula I by rectification. In the case where the product of formula I is nerol, preferred tertiary amines have a boiling point substantially lower than or higher than the boiling point of nerol, and particularly preferred ones have a boiling point of less than 180° C. at a pressure of 1 bar. The tertiary amine may be selected from those disclosed in EP 0 071 787 and is usually selected from tertiary aliphatic amines, such as optionally substituted trialkyl amines, e.g. trimethylamine, triethylamine, dimethylethylamine and triethanolamine, or optionally substituted N,N-dialkyl cycloalkylamines, e.g. N,N-dimethyl cyclohexylamine, N,N-dialkyl arylalkylamines, e.g. N,N-dimethylbenyzlamine, heterocyclic aromatic amines, e.g. pyridine, 3-chloropyridine, 2-methoxypyridine, collidine, 2,2'-bipyridine and phenanthroline, N-alkyl substituted heterocyclic amines, e.g. N-methyl piperidine and N-methyl morpholine, and tertiary mixed alkyl-aryl amines, such as N,N-dimethyl aniline.

According to a preferred embodiment of the present invention the tertiary amine is selected from tri($C_1$-$C_{20}$-alkyl)amines, more preferably from tri($C_1$-$C_5$-alkyl)amines, in particular from tri($C_1$-$C_3$-alkyl)amines, such as trimethylamine, triethylamine or N,N-dimethylethylamine, and specifically is trimethylamine.

The hydrogenation is typically carried out in a semi-continuous or discontinuous manner but, alternatively, may possibly also be conducted in a continuous manner. Preferably the hydrogenation is carried out discontinuously, i.e. in a batchwise manner.

The reactants, the catalyst and the tertiary amine can in principle be brought into contact with each other in any desired sequence. For example, the educt composition including the unsaturated aldehyde II can be initially charged and then the tertiary amine is added or, conversely, the tertiary amine can be initially charged and admixed with the aldehyde II, whereby the educt composition and the tertiary amine in each case may possibly be added in dissolved or dispersed form, if appropriate. Alternatively, the aldehyde II and the tertiary amine can also be charged simultaneously to the reaction vessel. The hydrogen gas is added before, after or during the addition of the aldehyde II or the tertiary amine by pressurizing the vessel. Similarly, the catalyst is added before, after or together with the aldehyde II or the tertiary amine.

It has been found to be favorable to minimize the residence time of the educt composition in the presence of the tertiary amine, in particular if the educt composition is citral. Therefore, in case the hydrogenation is effected in a discontinuous manner, the educt composition is preferably brought into contact with the tertiary amine not before or, at the earliest, immediately before the hydrogenation reaction is initiated, namely in particular, directly after, simultaneously with, or at most shortly before the initiation of the hydrogenation. Accordingly, in a preferred embodiment of the present invention the educt composition is contacted with the tertiary amine only after the vessel containing the catalyst has been purged with hydrogen gas and the desired reaction pressure and temperature within the vessel is reached. This can be accomplished for instance by adding the catalyst, purging and pressurizing the reaction vessel with hydrogen, setting the interior of the vessel to the desired temperature and adding either the educt composition or the tertiary amine in arbitrary sequence and only immediately thereafter adding the tertiary amine or the educt composition, respectively. In a particularly preferred embodiment the steps of adding the catalyst, purging and pressurizing the vessel with hydrogen and setting the interior temperature of the vessel are carried out in arbitrary sequence and then the educt composition and the tertiary amine are added separately from each other in direct succession. If it is necessary to bring the tertiary amine into contact with the educt composition before initiation of the hydrogenation, it is preferable to do so at a low temperature, such as less than 40° C.

As another measure for reducing the contact between the educt composition and the tertiary amine, the educt composition can be added to the reaction mixture continuously or intermittently over the course of the hydrogenation reaction. This way the intended full amount of the educt composition is not added in all at once but instead gradually over the period of the reaction.

According to further aspect of the present invention the two aforementioned measures for reducing the contact between the educt composition and the tertiary amine can also be applied in combination. Such an approach can be realized for instance by adding the catalyst, purging and pressurizing the reaction vessel with hydrogen and setting the interior temperature of the vessel in arbitrary sequence, then adding the tertiary amine and immediately thereafter starting to gradually add the educt composition.

The hydrogenation reaction of the inventive process may or may not be conducted in the presence of a solvent that is inert under hydrogenation conditions.

Preferably the hydrogenation is carried out in the presence of such a solvent, in particular a protic organic solvent. In a preferred embodiment of the present invention the organic solvent is selected from $C_1$-$C_8$-alkanoles, in particular from methanol, ethanol and isopropanol, and specifically is methanol.

Solvent is typically added to the hydrogenation reaction in an amount of 0 to 50% by weight, preferably in an amount of 5 to 40% by weight, in particular in an amount of 10 to 30% by weight and specifically in an amount of 15 to 25% by weight, relative in each case to the total weight of the liquid reaction mixture.

If a solvent is used in the hydrogenation reaction it is typically added together with the tertiary amine in the form of a solution obtained by dissolving the tertiary amine in the solvent.

In a preferred embodiment of the present invention the tertiary amine is used in an amount ranging from 0.005 to 0.5% by weight, in particular from 0.01 to 0.2% by weight and specifically from 0.05 to 0.15% by weight, relative in each case to the total amount of the liquid reaction mixture.

In another preferred embodiment of the present invention the catalyst used in hydrogenation of the inventive process is a supported catalyst as described herein before, especially a supported catalyst described herein as being preferred, that is used in an amount of 0.1 to 10% by weight, preferably 0.2 to 5% by weight, in particular 0.5 to 3% by weight and specifically 0.8 to 2% by weight, relative in each case to the total weight of the reaction mixture. In this context "reaction mixture" is meant to include the liquid as well as the solid constituents of the hydrogenation reaction mixture.

The hydrogenation is typically carried at a hydrogen pressure in the range from 1 to 250 bar, preferably in the range from 10 to 200 bar, more preferably in the rang e from 20 to 100 bar, in particular in the range from 30 to 75 bar and specifically in the range from 40 to 60 bar.

The hydrogen used for the hydrogenation can be used in pure form or, if desired, also in the form of mixtures with other, preferably inert gases, such as nitrogen or argon. Preference is given to using hydrogen in undiluted form.

The hydrogenation is typically carried at a temperature in the range from 10 to 200° C., preferably in the range from 10 to 200° C., more preferably in the range from 40 to 150° C., in particular in the range from 50 to 90° C. and specifically in the range of 60 to 80° C.

It is a particular benefit of the process of the invention that the activity of the catalyst, especially if it is a heterogeneous one, is usually not significantly changed during the hydrogenation carried out in a batch format. The catalyst, therefore, can be re-used in one or more subsequent discontinuous runs, i. e. the catalyst is recyclable. Particularly in the case of the aforementioned supported catalysts comprising ruthenium and iron it has even been found that one or more re-uses typically result in an improved selectivity of the catalysts. Thus, in a preferred embodiment of the present invention a heterogeneous catalyst is used in the inventive hydrogenation that is a recycled catalyst having been used in at least one, especially in at least two previous hydrogenation reactions.

The work-up of the reaction mixture obtained in the hydrogenation of the inventive process and the isolation of the product of the formula I are effected in a customary manner, for example by filtration, an aqueous extractive work-up or by a distillative separation, for example under reduced pressure. The product of formula I may be obtained in sufficient purity by applying such measures or a combination thereof, obviating additional purification steps. Alternatively, further purification can be accomplished by methods commonly used in the art, such as chromatography.

Preferably the work-up and the isolation of the product of the formula I are effected by filtering off the catalyst which then is typically recycled, removing volatile components, such as solvent and the tertiary amine, e.g. by evaporation and finally isolating the product of formula I by vacuum rectification.

In the process according to embodiment B of the present invention, in particular if citral is used as educt composition, a raw product is obtained which has a nerol content after hydrogenation, i.e. a nerol content after completion of the hydrogenation and subsequent removal of the catalyst as well as volatile components, of preferably more than 85% by weight, more preferably 90% by weight and in particular more than 92% by weight. In addition, said raw product has a geraniol content after hydrogenation of preferably not more than 9% by weight, more preferably not more than 6% by weight and in particular not more than 4% by weight.

In the process according to embodiment B of the present invention, in particular if citral is used as educt composition, the raw product obtained after completion of the hydrogenation has a nerol purity attainable by rectification, as defined herein before, of typically above 90%, preferably above 93%, more preferably above 94%, in particular above 95% and specifically above 96%. Accordingly, in a preferred embodiment of the invention the raw product obtained after the hydrogenation of the process according to embodiment B and possibly subsequent removal of the catalyst as well as of volatile components, is subjected to a rectification step affording nerol in a purity of above 90%, preferably above 93%, more preferably above 94%, in particular above 95% and specifically above 96%.

In a further preferred embodiment of the invention the raw product obtained in the hydrogenation of the process according to embodiment B and possibly subsequent removal of the catalyst as well as of volatile components, is subjected to a rectification step affording a nerol compound having a level of the by-products citronellol and nerol isomers of formulae III to V in total of less than 10% by weight, preferably less than 7% by weight, more preferably less than 6% by weight, in particular less than 5% by weight, specifically less than 4% by weight, such as particularly preferred in the range from 2 to 4% by weight, relative in each case to the total weight of the nerol compound.

In a further aspect, the present invention provides a nerol compound that is obtainable by the process of the invention after a final rectification step, in particular a nerol compound named hereunder "nerol compound A" which is characterized in that it comprises nerol in an amount exceeding 90% by weight, preferably exceeding 93% by weight, more preferably exceeding 95% by weight and specifically exceeding 96% by weight, relative in each case to the total weight of the nerol compound. In a preferred embodiment of the invention the nerol compound A comprises 94 to 98% by weight, preferably 95 to 98% by weight and more preferably 96 to 98% by weight, of nerol and 2 to 6% by weight, preferably 2 to 5% by weight and more preferably 2 to 4% by weight, of the by-products citronellol and nerol isomers of formulae III to V together, relative in each case to the total weight of the nerol compound.

With nerol compound A having a nerol content of at least above 90% by weight, a new compound is provided for use as an aroma chemical and particularly as odorant which holds very advantageous olfactory properties, in that it is suitable for producing scents with rose-floral and fresh, citrus-like notes.

Thus, a preferred embodiment of the present invention is directed to uses of the nerol compound A obtainable by the inventive process as an aroma chemical and especially as an odorant. Particular preference is given to such uses of the nerol compound A in compositions to be flavored or odorized, for instance perfumes, detergents and cleaners, cosmetic compositions, bodycare compositions, hygiene articles, products for oral and dental hygiene, scent dispensers and fragrances. Particular preference is also given to such uses of the nerol compound A for producing a radiant and impactful rose-floral note that is fresh, citrusy, powdery, and smooth, in particular in a composition to be flavored or odorized, such as one of those mentioned above.

In a further aspect, the present invention provides a fragrance or aroma substance composition, comprising
a) the nerol compound A obtainable by the inventive process,
b) optionally at least one further aroma chemical different from component a), and
c) optionally at least one diluent,
with the proviso that the composition comprises at least one of the components b) or c).

Preferably the fragrance or aroma substance composition according to the invention comprises the component a) in a weight fraction of from 0.1 to 95% by weight, more preferably from 0.1 to 90% by weight and in particular from 0.1 to 80% by weight, based on the total weight of the composition.

More preferably, the fragrance or aroma substance composition according to the invention comprises the component a) in a weight fraction of from 0.1 to 70% by weight, more preferably 1 to 50% by weight, based on the total weight of the composition. In a specific embodiment, the fragrance or aroma substance composition according to the invention comprises the component a) in a weight fraction of from 2 to 30% by weight, more specifically 3 to 15% by weight, based on the total weight of the composition.

The fragrance or aroma substance compositions of the present invention may also optionally comprise as component b) one or more additional fragrance substance(s) different from component a). The fragrance or aroma substance compositions of the present invention may also optionally comprise as component c) one or more diluent(s). Furthermore, the fragrance or aroma substance compositions of the present invention may also optionally comprise further constituents known to those of skill in the art as common ingredients in fragrance or aroma substance compositions.

In a preferred embodiment, the fragrance or aroma substance composition according to the invention comprises the component a) as the sole aroma chemical.

In a further preferred embodiment, the fragrance or aroma substance composition according to the invention comprises as component b) at least one further aroma chemical besides the nerol compound A obtainable by the inventive process.

Examples of substances that are suitable to be included in the inventive fragrance or aroma substance composition as optional aroma chemicals of component b) can be found for example in S. Arctander, Perfume and Flavor Materials, Vol. I and II, Montclair, N.J., 1969, selfpublished, or in K. Bauer, D. Garbe and H. Surburg, Common Fragrance and Flavor Materials, 4th edition, Wiley-VCH, Weinheim 2001, such as for instance the following substances:

extracts from natural raw materials such as essential oils, concretes, absolutes, resins, resinoids, balsams, tinctures such as e.g. ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; ylang ylang oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; citronellol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethylacetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; alpha-damascenone; beta-damascone; beta-damascenone; delta-damascone; delta-damascenone; gamma-damascone; gamma-damascenone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethyl-cyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; dihydrorose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9-cyclo-heptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropyl phenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylaceto-phenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate; the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanenitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropyl-pyrazine; 2-isobutyl-3-methoxy-pyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the rose pyranes such as e.g. tetrahydro-4-methyl-2-phenyl-2H-pyrane; 3,6-dihydro-4-methyl-2-phenyl-2H-pyrane;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The further aroma chemical that besides the nerol compound A may optionally be also included in the fragrance or aroma substance composition of the invention is preferably selected from the known range of substances having a floral and/or herbal rose scent, such as in particular natural rose oils, rose oxide, dihydrorose oxide, the nerol isomers of formulae III to V, geraniol, diphenyl ether, rose pyranes such as e.g. tetrahydro-4-methyl-2-phenyl-2H-pyrane and 3,6-dihydro-4-methyl-2-phenyl-2H-pyrane, 3-methyl-5-phenyl-pentanol, alpha-damascone, alpha-damascenone, beta-damascone, beta-damascenone, delta-damascone, delta-damascenone, gamma-damascone, gamma-damascenone and citronellol.

If a component b) is present at all in the fragrance or aroma substance composition of the invention, the weight ratio of component a) to component b), is preferably in a range from 100:1 to 1:100, more preferably from 50:1 to 1:50 and in particular from 25:1 to 1:25.

The fragrance or aroma substance composition can optionally comprise at least one diluent of component c). Suitable diluents can be used individually or as a mixture of two or more diluents. Suitable diluents are those as are customarily used as solvents for fragrances or flavors.

Preferably, the fragrance or aroma substance composition comprises, as diluent(s) of component c), at least one compound which is liquid at 20° C. and 1013 mbar.

It is also preferred that the nerol compound A of component a) has a solubility in component c), if present, of at least 0.1 mg/ml at 20° C., particularly preferably of at least 0.5 mg/ml at 20° C. In addition, the one or more compounds of component b), if present, preferably have solubilities in component c) of at least 0.1 mg/ml at 20° C., in particular of at least 0.5 mg/ml at 20° C.

The diluent(s) of component c) are preferably selected from aliphatic and cycloaliphatic mono-alcohols, polyols, open-chain aliphatic ethers, cyclic ethers, polyol mono- and polyethers, esters and mixtures thereof.

Suitable aliphatic and cycloaliphatic mono-alcohols are e.g. ethanol, n-propanol, isopropanol, n-butanol, sec-butanol, tert-butanol and cyclohexanol.

Suitable polyols are e.g. ethylene glycol, propylene glycol, 1,2-butylene glycol, diethylene glycol, dipropylene glycol or glycerol.

Suitable open-chain aliphatic ethers and cyclic ethers are e.g. diethyl ether, dipropyl ether, diisopropyl ether, methyl tert-butyl ether, tetrahydrofuran, tetrahydropyran, 1,4-dioxane or morpholine.

Suitable polyol mono- and polyethers are e.g. ethylene glycol monomethyl ether, ethylene glycol dimethyl ether, ethylene glycol monoethyl ether, ethylene glycol diethyl ether, propylene glycol monoethyl ether, propylene glycol diethyl ether or diethylene glycol monoethyl ether.

Suitable esters are ethyl acetate, methyl acetate, propyl acetate, isopropyl acetate, n-butyl acetate, sec-butyl acetate, tert-butyl acetate, isobutyl acetate, isoamyl acetate, ethyl butyrates, ethyl lactate, diethyl carbonate, ethylene carbonates, propylene carbonate, triethyl citrate, isopropyl myristate, diethyl phthalate, dialkyl esters of 1,2-cyclohexanedicarboxylic acid, specifically 1,2-cyclohexanedicarboxylic acid diisononyl ester (Hexamoll® DINCH, BASF SE), etc.

The present invention also provides a method for imparting and/or intensifying an odor or flavor of a product with a fresh, citrusy, powdery and smooth rose-floral note, in which the product is brought into contact with an organoleptically effective amount of the nerol compound A that is obtainable by the inventive process.

Pursuant to this method the contacting of the product with the nerol compound A is achieved by incorporating the nerol compound A into the product and or by applying it to the product using procedures well-known in the art for such purposes. In this context the nerol compound A may be used in neat form or in the form of the fragrance or aroma substance composition of the invention.

In the context of the present invention, an organoleptically effective amount is to be understood as meaning an amount which suffices, upon application as intended, to bring about a scent impression for the user or consumer. When using the nerol compound A as obtainable by the inventive process, this is specifically the impression of a pleasant citrusy odor with a rose-floral note.

The present invention additionally provides a perfumed or aromatized product, comprising an organoleptically effective amount of the nerol compound A as obtainable by the inventive process, or comprising an organoleptically effective amount of the inventive fragrance or aroma substance composition as defined herein before. Said perfumed or aromatized product is preferably obtained by the aforementioned method for imparting and/or intensifying an odor or flavor of a product.

By means of the aforementioned inventive method in principle any desired product can be perfumed or aromatized. In this regard perfumed or aromatized products as well as products to be perfumed or aromatized are preferably selected from scent dispensers and fragrance perfumes, detergents and cleaners, cosmetic compositions, body care compositions, hygiene articles, products for oral and dental hygiene, pharmaceutical compositions and crop protection compositions. Examples for these product groups are given in the following.

Examples of scent dispensers are for instance air fresheners in a liquid or a gel-like form which may be adsorbed to a solid carrier.

Examples of fragrance perfumes are for instance perfume extracts, Eau de Parfums, Eau de Toilettes, Eau de Colognes, Eau de Solide, Extrait Parfum, aerosol sprays, scented cleaners and oils.

Examples of detergents are for instance liquid detergents, powder detergents, laundry pretreatments such as bleaches, soaking agents and stain removers, fabric softeners, washing soaps and washing tablets.

Examples of cleaners are for instance perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, lime scale removers, grill and oven cleaners, algae and moss removers, mold removers and facade cleaners.

Examples of cosmetic compositions are for instance cosmetic emulsions of the oil-in-water type, of the water-in-oil type and of the water-in-oil-in-water type, such as e.g. skin creams and lotions, face creams and lotions, sunscreen creams and lotions, after sun creams and lotions, hand creams and lotions, foot creams and lotions, hair removal creams and lotions, aftershave creams and lotions, tanning creams and lotions, and also decorative cosmetics such as e.g. eyeshadows, nail varnishes, make-ups, lipsticks and mascara.

Examples of body care compositions are for instance aftershaves, pre-shave products, splash colognes, solid and liquid soaps, shower gels, shampoos, shaving soaps, saving foams, bath oils, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams.

Examples of hygiene articles are for instance candles, lamp oils, joss sticks, insecticides, repellents, propellants, rust removers, perfumed freshening wipes, armpit pads, baby diapers, sanitary towels, toilet paper, cosmetic wipes, pocket tissues and dishwasher deodorizer;

Examples of products for oral and dental hygiene are for instance toothpaste and dental floss.

Examples of pharmaceutical composition are any compositions useful for treating humans or animals, while examples of crop protection compositions are any compositions useful to protect crops in particular against weeds, insects and/or fungi.

The examples below serve to illustrate the invention without limiting it in any way.

EXAMPLES

Preparation of Supported Catalysts

Example 1: Preparation of Catalyst A (in Analogy to EP 1 317 959, Example 1D)

110 g of the activated carbon Norit SX Plus® were introduced without further pretreatment into a stirred flask with 2 L of water, suspended and heated to 80° C. under reflux. The pH was then raised to 9 by adding aqueous NaOH (1 mol/l). Within one hour, 300 mL of a solution of ruthenium nitrosyl nitrate and iron nitrate (concentration corresponding to 5.85 g of Ru and 1.17 g of Fe) are added dropwise at 80° C. while at the same time maintaining the pH at about 9 by simultaneously adding aqueous NaOH. Stirring was continued at 80° C. for one hour and then the mixture was cooled. The cold suspension was filtered and washed with 40 L of water, then dried in a vacuum drying cabinet at 80° C. for 16 h. The dried powder was then reduced in a rotary sphere oven in a stream consisting of 70% hydrogen and 30% nitrogen at 500° C. for 3 h. After the end of the reduction, cooling was carried out under nitrogen and the catalyst was passivated with a gas mixture of 1% oxygen in nitrogen. The catalyst had a Ru content of 5.0% by weight, an Fe content of 1.0% by weight and an Na content of 0.036% by weight.

Example 2: Preparation of Catalyst B (in analogy to unpublished patent application EP 1588361.8, example 1D) 110 g of the activated carbon Norit SX Plus® were introduced without further pretreatment into a stirred flask with 2 L of water, suspended and heated to 80° C. under reflux. The pH was then raised to 9 by adding aqueous NaOH (1 mol/l). Within one hour, 300 mL of a solution of ruthenium nitrosyl nitrate and iron nitrate (concentration corresponding to 5.85 g of Ru and 1.17 g of Fe) are added dropwise at 80° C. while at the same time maintaining the pH at about 9 by simultaneously adding aqueous NaOH. Stirring was continued at 80° C. for one hour and then the mixture was cooled. The cold suspension was filtered and washed with 40 L of water, then dried in a vacuum drying cabinet at 80° C. for 16 h. The dried powder was then reduced in a rotary sphere oven in a stream consisting of 70% hydrogen and 30% nitrogen at 200° C. for 3 h. After the end of the reduction, cooling was carried out under nitrogen and the catalyst was passivated with a gas mixture of 1% oxygen in nitrogen. The catalyst had a Ru content of 5.0% by weight, an Fe content of 1.0% by weight and an Na content of 0.036% by weight.

The Catalysts A and B prepared in Examples 1 and 2 were employed in the following hydrogenation reactions only in recycled form after being used in at least two successive hydrogenations (with the exception of Comparative Example 3).

Hydrogenations of Citral

GC analyses were performed using a Stabilwax column from Restek with a length of 60 m, an inner diameter of 0.32 mm and a film thickness of 1.0 µm, an injector temperature of 260° C., an FID detector with a detector temperature of 300° C., and the oven program: 125° C. start temperature, ramp 5° C./min increase to 160° C., 30 min isothermal, ramp 10° C./min increase to 235° C., 20 min isothermal.

Example 3

To an autoclave with an interior volume of 300 mL containing recycled Catalyst B (2.4 g), citral (120 g), comprising 98.4% neral and 0.2% geranial (area % measured by GC), and a solution of trimethylamine (150 mg) in methanol (29.9 g) were added separately and in direct succession. Hydrogen was introduced into the autoclave immediately thereafter until a pressure of 50 bar was reached and then the hydrogen flow was initially set to 16 standard liter per hour (sl/h). Simultaneously, the stirrer was switched on and the interior temperature was adjusted to 70° C. The excess hydrogen was continuously released via an exhaust valve. After one hour the hydrogen flow was reduced to 6 sl/h and after six additional hours the hydrogenation was terminated by removing the reaction mixture from the autoclave by filtering it through a frit. The raw product obtained following removal of volatile components, such as methanol and trimethylamine, by evaporation had the following composition (in area % measured by GC: neral: 0.2%, geranial: 0.1%, citronellol: 2.2%, nerol isomers: 2.3%, nerol 85.5%, geraniol: 8.5%. The nerol content after hydrogenation, as defined herein previously, was 85.5%. The nerol purity attainable by rectification, as defined herein previously, was 95.0%.

Example 4

Three hydrogenations were carried out according to the following procedure at a temperature of 60° C., 70° C. and 80° C., respectively.

To an autoclave with an interior volume of 300 mL containing recycled Catalyst B (2.4 g), hydrogen was introduced until a pressure of 50 bar was reached. Then the hydrogen flow was initially set to 16 sl/h. Meanwhile, the stirrer was switched on and the heater was set to the intended temperature. Once the respectively desired temperature was reached, citral (120 g), comprising 99.2% neral and 0.1% geranial, and a solution of trimethylamine (150 mg) in methanol (29.9 g) were added separately and in direct succession to the autoclave. The excess hydrogen was continuously released via an exhaust valve. After one hour the hydrogen flow was reduced to 6 sl/h and after six additional hours the hydrogenation was terminated by removing the reaction mixture from the autoclave by filtering it through a frit. The raw product obtained in each case following removal of volatile components, such as methanol and trimethylamine, by evaporation had the composition listed in the following table 1 (in area % measured by GC).

TABLE 1

| Reaction temperature: | 60° C. | 70° C. | 80° C. |
|---|---|---|---|
| neral: | <0.1 | <0.1 | <0.1 |
| geranial: | <0.1 | <0.1 | <0.1 |
| citronellol: | 2.1 | 2.1 | 2.9 |
| nerol isomers: | 1.1 | 1.6 | 1.7 |
| nerol *): | 90.6 | 87.4 | 87.5 |
| geraniol: | 5.2 | 7.5 | 6.4 |
| nerol purity **): | 96.6 | 95.9 | 95.0 |

*) nerol content after hydrogenation, as defined herein previously,
**) nerol purity attainable by rectification, as defined herein previously.

Example 5

A test series was carried out, wherein the same catalyst was used three times not according to the invention, then in 29 consecutive hydrogenations, all according to the invention.

The first three hydrogenations (not according to the invention) were carried out as follows:

To an autoclave with an interior volume of 300 mL containing Catalyst B (2.4 g), citral (120 g), comprising 48.0% neral and 48.4% geranial, and a solution of trimethylamine (5 g) in methanol (25 g) were added separately and in direct succession. Immediately thereafter hydrogen was introduced into the autoclave until a pressure of 50 bar was reached and then the hydrogen flow was initially set to 16 sl/h. Meanwhile, the stirrer was switched on and the heater was set such that after about 45 minutes the desired interior temperature of 70° C. was reached. After one hour the hydrogen flow was reduced to 6 sl/h. The excess hydrogen was continuously released via an exhaust valve. The hydrogenation was then terminated after a total reaction time of 4-5 hours by removing the reaction mixture from the autoclave by filtering it through a frit. The raw products obtained following removal of volatile components, such as methanol and trimethylamine, by evaporation had the compositions listed in the following table 2, runs 1, 2, and 3 (in area % measured by GC).

The subsequent hydrogenations according to the invention were conducted as follows:

An autoclave with an interior volume of 300 mL containing recycled Catalyst B (2.4 g) was added citral (120 g) comprising 99.1% neral and 0.2% geranial. A solution of trimethylamine (150 mg) in methanol (29.9 g) were added separately and in direct succession to the autoclave. Immediately thereafter hydrogen was introduced into the autoclave until a pressure of 50 bar was reached and then the hydrogen flow was initially set to 16 sl/h. Meanwhile, the stirrer was switched on and the heater was set such that after about 45 minutes the desired interior temperature of 70° C. was reached. After one to three hours the hydrogen flow was reduced to 6 sl/h (in runs 12, 13 and 14 the hydrogen flow was later reduced to 3 sl/h). The excess hydrogen was continuously released via an exhaust valve. The hydrogenation was then terminated after a total reaction time of 7 hours by removing the reaction mixture from the autoclave by filtering it through a frit. The raw products obtained in the fourth, fifth, sixth, fifteenth, twentieth, and thirtieth run following removal of volatile components, such as methanol and trimethylamine, by evaporation had the compositions listed in the following table 2 (in area % measured by GC).

TABLE 2

| No. of run: | 1 #) | 2 #) | 3 #) | 4 | 5 | 6 | 15 | 20 | 30 |
|---|---|---|---|---|---|---|---|---|---|
| neral: | <0.1 | <0.1 | <0.1 | <0.1 | <0.1 | <0.1 | <0.1 | <0.1 | 0.2 |
| geranial: | <0.1 | <0.1 | <0.1 | <0.1 | <0.1 | <0.1 | <0.1 | <0.1 | <0.1 |
| citronellol: | 17.7 | 3.2 | 2.1 | 3.1 | 3.6 | 3.4 | 2.0 | 1.9 | 1.7 |
| nerol isomers: | 1.2 | 1.6 | 1.7 | 1.3 | 1.2 | 1.3 | 1.7 | 1.9 | 2.2 |
| nerol *): | 36.2 | 41.2 | 40.3 | 88.2 | 90.4 | 90.2 | 89.0 | 86.8 | 87.1 |
| geraniol: | 43.4 | 51.2 | 53.5 | 6.5 | 3.9 | 4.0 | 6.3 | 7.8 | 7.9 |
| nerol purity **): | 65.7 | 89.5 | 91.4 | 95.2 | 95.0 | 95.0 | 96.0 | 95.8 | 95.8 |

) not according to the invention,
*) nerol content after hydrogenation, as defined herein previously,
**) nerol purity attainable by rectification, as defined herein previously.

It can be seen from table 2 that the activity of the catalyst remained practically unchanged through all 30 hydrogenation runs while its specificity underwent only minor changes, as evident from both, the consistently near-complete consumptions of neral and the consistently excellent nerol purities attainable by rectification.

Example 6

To an autoclave with an interior volume of 300 mL was charged recycled Catalyst A (2.3 g), hydrogen was afterwards introduced into the autoclave until a pressure of 50 bar was reached. Then the hydrogen flow was set to 16 sl/h. Meanwhile, the stirrer was switched on and the interior temperature was adjusted to 70° C. Subsequently a first portion of citral (30 g), comprising 99.2% neral and 0.1% geranial, and a solution of trimethylamine (180 mg) in methanol (29.8 g) were added separately and in direct succession to the autoclave. Additional portions of citral (3×30 g) were introduced after a reaction time of 1.5 hours, 3 hours and 4.5 hours, respectively, into the autoclave. The excess hydrogen was continuously released via an exhaust valve. After a total reaction time of seven hours the hydrogenation was terminated by removing the reaction mixture from the autoclave by filtering it through a frit. The raw product obtained following removal of volatile components, such as methanol and trimethylamine, by evaporation had the following composition (in area % measured by GC): neral: 0.6%, geranial: 0.0%, citronellol: 2.8%, nerol isomers: 1.6%, nerol 90.0%, geraniol: 3.9%. The nerol content after hydrogenation, as defined herein previously, was 90.0%. The nerol purity attainable by rectification, as defined herein previously, was 95.3%. Subsequently, the raw product was rectified using a spinning band column at a still temperature of 117-118° C., a head vacuum of 20 mbar and a reflux to distillate ratio of 5:1. The nerol fraction was collected at a head temperature of 115° C.

The olfactory assessment of the nerol fraction by a perfumer revealed a nerol scent of good quality with a warm geraniol effect.

Example 7

To an autoclave with an interior volume of 300 mL was charged recycled Catalyst A (2.3 g), hydrogen was afterwards introduced into the autoclave until a pressure of 50 bar was reached. Then the hydrogen flow was set to 16 sl/h. Meanwhile, the stirrer was switched on and the interior temperature was adjusted to 70° C. Subsequently a first portion of citral (30 g), comprising 99.2% neral and 0.1% geranial, and a solution of trimethylamine (180 mg) in methanol (29.8 g) were added separately and in direct succession to the autoclave. Additional portions of citral (3×30 g) were introduced after a reaction time of 1.5 hours, 3 hours and 4.5 hours, respectively, into the autoclave. The excess hydrogen was continuously released via an exhaust valve. After a total reaction time of 6.5 hours the hydrogenation was terminated by removing the reaction mixture from the autoclave by filtering it through a frit. The raw product obtained following removal of volatile components, such as methanol and trimethylamine, by evaporation had the following composition (in area % measured by GC): neral: 2.9%, geranial: 0.0%, citronellol: 2.4%, nerol isomers: 1.3%, nerol 87.9%, geraniol: 4.4%. The nerol content after hydrogenation, as defined herein previously, was 87.9%. The nerol purity attainable by rectification, as defined herein previously, was 95.9%. Subsequently, the raw product was rectified using a spinning band column at a still temperature of 121° C., a head vacuum of 20 mbar and a reflux to distillate ratio of 10:1. The nerol fraction was collected at a head temperature of 114° C.

The olfactory assessment of the nerol fraction by a perfumer revealed a nerol scent of good quality that is round and rosy as well as very long lasting.

Example 8

Three hydrogenations were carried out according to the following procedure using trimethylamine in an amount of 1.77, 0.59 and 0.24% by weight, respectively.

To an autoclave with an interior volume of 300 mL containing Catalyst A (2.3 g) hydrogen was introduced until a pressure of 50 bar was reached. The hydrogen flow was initially set to 16 sl/h. Meanwhile, the stirrer was switched on and the heater was set to 70° C. Once an interior temperature of 70° C. was reached, citral (120 g), comprising 99.2% neral and 0.1% geranial, and a solution (30 g) of trimethylamine (2.7, 0.9 or 0.36 g) in methanol were added separately and in direct succession to the autoclave. After 1.5 hours or, in the case 0.36 g of trimethylamine were used, 2.5 hours the hydrogen flow was reduced to 6 sl/h. The excess hydrogen was released via an exhaust valve. The hydrogenation was terminated after a total reaction time of 7 hours by removing the reaction mixture from the autoclave by filtering it through a frit. The raw product obtained in each case following removal of volatile components, such as methanol and trimethylamine, by evaporation had the composition listed in the following table 3 (in area % measured by GC).

TABLE 3

| Amount of trimethylamine: | 1.77 wt-% #) | 0.59 wt-% | 0.24 wt-% |
| --- | --- | --- | --- |
| neral: | 0 | 0 | 0.1 |
| geranial: | 0 | 0 | <0.1 |
| citronellol: | 3.7 | 3.4 | 3.3 |
| nerol isomers: | 1.9 | 1.8 | 1.8 |
| nerol *): | 70.2 | 79.6 | 83.8 |
| geraniol: | 23.3 | 14.3 | 10.2 |
| nerol purity **): | 92.6 | 93.9 | 94.3 |

) not according to the invention,
*) nerol content after hydrogenation, as defined herein previously,
**) nerol purity attainable by rectification, as defined herein previously.

It is apparent from table 3 that reduced amounts of trimethylamine result in markedly higher yields of the desired nerol and lower yields of the undesired geraniol, with the yield of nerol increasing to about the same extent as the yield of geranial decreased. Thus, in particular quantities of trimethylamine above 1% by weight, relative to the total amount of the liquid reaction mixture, lead to substantially higher rates of the unwanted by-product geranial, due to a largely enhanced E/Z-isomerization of the conjugated double bond.

Comparative Example 1

To an autoclave with an interior volume of 300 mL containing Catalyst A (2.3 g) hydrogen was introduced until a pressure of 50 bar was reached. The hydrogen flow was initially set to 16 sl/h. Meanwhile, the stirrer was switched on and the heater was set to 70° C. Once an interior temperature of 70° C. was reached, citral (120 g), comprising 99.2% neral and 0.1% geranial, and a solution of trimethylamine (1.8 g) in methanol (28.2 g) were added separately and in direct succession to the autoclave. After 1.5 hours the hydrogen flow was reduced to 6 sl/h. The excess hydrogen was continuously released via an exhaust valve. After 3.5 additional hours the hydrogenation was terminated by removing the reaction mixture from the autoclave by filtering it through a frit. The raw product obtained following removal of volatile components, such as methanol and trimethylamine, by evaporation had the following composition (in area % measured by GC): neral: 0.0%, geranial: 0.0%, citronellol: 2.9%, nerol isomers: 2.0%, nerol 73.4%, geraniol: 20.9%. The nerol content after hydrogenation, as defined herein previously, was 73.4%. The nerol purity attainable by rectification, as defined herein previously, was 93.7%.

Comparative Example 2

To an autoclave with an interior volume of 300 mL containing recycled Catalyst A (2.3 g) were charged citral (120 g), comprising 99.2% neral and 0.1% geranial, and a solution of trimethylamine (5.4 g) in methanol (24.6 g) separately and in direct succession. Immediately thereafter hydrogen was introduced into the autoclave until a pressure of 50 bar was reached and then the hydrogen flow was initially set to 16 sl/h. Meanwhile, the stirrer was switched on and the interior temperature was adjusted to 70° C. After 1.5 hours the hydrogen flow was reduced to 6 sl/h. The excess hydrogen was continuously released via an exhaust valve. The hydrogenation was then terminated after a total reaction time of 6 hours by removing the reaction mixture from the autoclave by filtering it through a frit. The raw product obtained following removal of volatile components, such as methanol and trimethylamine, by evaporation had the following composition (in area % measured by GC): neral: 0.0%, geranial: 0.0%, citronellol: 3.1%, nerol isomers: 1.9%, nerol 62.9%, geraniol: 31.5%. The nerol content after hydrogenation, as defined herein previously, was 62.9%. The nerol purity attainable by rectification, as defined herein previously, was 92.8%.

As can be seen from Comparative Examples 1 and 2 the use of higher amounts of trimethylamine than required according to the present invention resulted in a markedly decreased specificity of the hydrogenation reaction and, thus, in an inacceptable low yield of nerol. Also, the nerol purities attainable by rectification were not very good.

Comparative Example 3

An autoclave with an interior volume of 300 mL containing Catalyst A (2.3 g) hydrogen was introduced until a pressure of 50 bar was reached. The hydrogen flow was initially set to 16 sl/h. Meanwhile, the stirrer was switched on and the heater was set to 100° C. Once an interior temperature of 100° C. was reached, citral (109 g, 70.0% by volume), comprising 99.2% neral and 0.1% geranial and a solution of trimethylamine (3.3 g, 3.0% by volume) in methanol (37.3 g, 27.0% by volume) were added separately and in direct succession to the autoclave. The excess hydrogen was released via an exhaust valve. The hydrogenation was terminated after a total reaction time of 1.2 hours by removing the reaction mixture from the autoclave by filtering it through a frit. The raw product obtained following removal of volatile components, such as methanol and trimethylamine, by evaporation had the following composition (in area % measured by GC): neral 0.3%, geranial: 0.1%, citronellol: 3.3%, nerol isomers: 3.1%, nerol 54.4%, geraniol: 37.2%. The nerol purity attainable by rectification, as defined herein before, was 89.5%.

Comparative Example 3 corresponds to the working example of EP 1 317 959 which describes a discontinuous hydrogenation of citral using trimethylamine in an amount of 3% by volume. As can be seen from the data given above the high trimethylamine content results in a very low yield of nerol due to its largely increased isomerization to geraniol.

Comparative Example 4

A test series was carried, where the same catalyst was used in 7 consecutive hydrogenations.

The first six hydrogenations were conducted as follows:

To an autoclave with an interior volume of 300 mL was charged fresh Catalyst B (2.4 g) and then hydrogen was introduced until a pressure of 50 bar was reached. The hydrogen flow was initially set to 16 sl/h. Meanwhile, the stirrer and the heater were switched on. Once an interior temperature of 70° C. was reached, citral (120 g), comprising 98.6% neral and 0.6% geranial, and methanol (30 g) were added separately and in direct succession to the autoclave. The excess hydrogen was continuously released via an exhaust valve. After one hour the hydrogen flow was reduced to 6 sl/h and after six additional hours the hydrogenation was terminated by removing the reaction mixture from the autoclave by filtering it through a frit. The raw product obtained in each of the hydrogenation runs following removal of volatile components, such as methanol and trimethylamine, by evaporation had the composition listed in the following table 4 (in area % measured by GC).

The seventh hydrogenation is according to the invention and was conducted as follows:

To an autoclave with an interior volume of 300 mL containing recycled Catalyst B (2.4 g), hydrogen was introduced until a pressure of 50 bar was reached. The hydrogen flow was initially set to 16 sl/h. Meanwhile, the stirrer and the heater were switched on. Once an interior temperature of 70° C. was reached, citral (120 g), comprising 98.6% neral and 0.6% geranial, and a solution of trimethylamine (180 mg) and methanol (29.8 g) were added separately and in direct succession to the autoclave. The excess hydrogen was continuously released via an exhaust valve. After one hour the hydrogen flow was reduced to 6 sl/h and after six additional hours the hydrogenation was terminated by removing the reaction mixture from the autoclave by filtering it through a frit. The raw product obtained following removal of volatile components, such as methanol and trimethylamine, by evaporation had the composition listed in the following table 4 (in area % measured by GC).

TABLE 4

| No. of run: | 1 [#] | 2 [#] | 3 [#] | 4 [#] | 5 [#] | 6 [#] | 7 [##] |
|---|---|---|---|---|---|---|---|
| neral: | <0.1 | <0.1 | 0.3 | 0.3 | 0.9 | 3.6 | <0.1 |
| geranial: | <0.1 | <0.1 | <0.1 | <0.1 | <0.1 | <0.1 | <0.1 |
| citronellol: | 16.2 | 17.7 | 5.5 | 4.3 | 3.7 | 3.0 | 1.8 |
| nerol isomers: | 1.2 | 1.2 | 1.4 | 1.4 | 1.4 | 1.5 | 2.6 |
| nerol [*]: | 75.5 | 72.7 | 90.6 | 92.0 | 91.6 | 88.8 | 90.8 |
| geraniol: | 1.5 | 0.8 | 0.8 | 0.8 | 0.8 | 0.8 | 4.0 |
| nerol purity [**]: | 81.9 | 79.4 | 92.9 | 94.2 | 95.2 | 95.4 | 95.4 |

[#] not according to the invention,
[##] according to the invention,
[*] nerol content after hydrogenation, as defined herein previously,
[**] nerol purity attainable by rectification, as defined herein previously.

It can be seen from table 4 that the omission of a tertiary amine led to a sharp decrease of the catalyst's activity, since the neral consumption rates distinctly declined after the fourth hydrogenation run. It can also been seen that adding a small amount of trimethylamine in accordance to the inventive process restored the activity of the catalyst.

The invention claimed is:

1. A process for the preparation of an unsaturated alcohol of the formula (I),

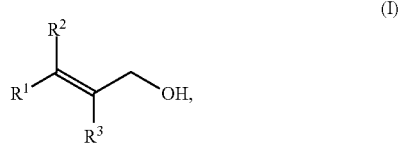

(I)

wherein
one of $R^1$ and $R^2$ is $C_4$-$C_{10}$-alkenyl containing one double bond and the other one is methyl; and
$R^3$ is selected from hydrogen;
which comprises subjecting an educt composition including at least 75% by weight of an unsaturated aldehyde of the formula (II)

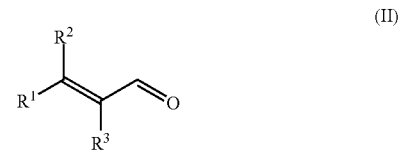

(II)

wherein $R^1$, $R^2$ and $R^3$ have the above defined meanings, to a hydrogenation in the presence of a catalyst and a tertiary amine in a liquid mixture; and
wherein the tertiary amine is used in an amount ranging from 0.001 to 0.5% by weight, based on the total amount of the liquid reaction mixture.

2. The process according to claim 1, wherein the catalyst is a heterogeneous catalyst.

3. The process according to claim 2, wherein the heterogeneous catalyst is a supported catalyst which comprises ruthenium as supported on an inert support material.

4. The process according to claim 3, wherein the supported catalyst additionally comprises iron.

5. The process according to claim 1, wherein the tertiary amine is used in an amount ranging from 0.005 to 0.5% by weight based on the total amount of the liquid reaction mixture.

6. The process according to claim 1, wherein the tertiary amine is selected from tri($C_1$-$C_{20}$-alkyl)amine.

7. The process according to claim 1, wherein the unsaturated alcohol of the formula (I) is geraniol and the unsaturated aldehyde of the formula (II) is geranial.

8. The process according to claim 1, wherein the unsaturated alcohol of the formula (I) is nerol and the unsaturated aldehyde of the formula (II) is neral.

9. The process according to claim 8, wherein the educt composition is citral, which comprises at least 90% by weight of neral.

10. The process according to claim 9, wherein the raw product obtained has a nerol content after hydrogenation of more than 90% by weight, and a geraniol content after hydrogenation of not more than 9% by weight.

11. The process according to claim 8, wherein the raw product obtained after the hydrogenation is subjected to a rectification step affording nerol in a purity of above 90%.

12. The process according to claim 8, wherein the raw product obtained after the hydrogenation is subjected to a rectification step affording a nerol compound having a level of the by-products citronellol and nerol isomers in total of less than 10% by weight.

13. The process according to claim 1, wherein the tertiary amine is trimethylamine and the trimethylamine is used in an amount ranging 0.01 to 0.2% by weight, based on the total amount of the liquid reaction mixture.

14. The process according to claim 8, wherein the educt composition is citral, which comprises at least 99% by weight of neral and wherein the raw product obtained has a nerol content after hydrogenation of more than 90% by weight, and a geraniol content after hydrogenation of not more than 6% by weight.

15. The process according to claim 8, wherein the raw product obtained after the hydrogenation is subjected to a rectification step affording a nerol compound having a level of the by-products citronellol and nerol isomers in total from 2 to 4% by weight.

16. The process according to claim 14, wherein the tertiary amine is trimethylamine and the trimethylamine is used in an amount ranging 0.01 to 0.2% by weight, based on the total amount of the liquid reaction mixture.

17. The process according to claim 16, wherein the raw product obtained after the hydrogenation is subjected to a rectification step affording nerol in a purity of above 94%.

18. The process according to claim 1, wherein the tertiary amine is used in an amount ranging 0.01 to 0.2% by weight, based on the total amount of the liquid reaction mixture.

19. The process according to claim 1, wherein the tertiary amine is trimethyl amine.

* * * * *